(12) United States Patent
Maritan et al.

(10) Patent No.: US 11,013,865 B2
(45) Date of Patent: May 25, 2021

(54) TIP CAP ASSEMBLY FOR CLOSING AN INJECTION SYSTEM

(71) Applicant: Becton Dickinson France, Le Pont de Claix (FR)

(72) Inventors: Lionel Maritan, Pierre-Chatel (FR); Franck Carrel, Saint Jean de Vaulx (FR)

(73) Assignee: Becton Dickinson France, Le Pont de Claix (FR)

( * ) Notice: Subject to any disclaimer, the term of this patent is extended or adjusted under 35 U.S.C. 154(b) by 448 days.

(21) Appl. No.: 15/028,950

(22) PCT Filed: Oct. 14, 2014

(86) PCT No.: PCT/EP2014/071950
§ 371 (c)(1),
(2) Date: Apr. 13, 2016

(87) PCT Pub. No.: WO2015/055608
PCT Pub. Date: Apr. 23, 2015

(65) Prior Publication Data
US 2016/0250420 A1    Sep. 1, 2016

(30) Foreign Application Priority Data
Oct. 15, 2013   (EP) ..................... 13306414

(51) Int. Cl.
*A61M 5/32*   (2006.01)
*A61M 5/34*   (2006.01)
(Continued)

(52) U.S. Cl.
CPC .......... *A61M 5/3202* (2013.01); *A61M 5/347* (2013.01); *A61M 5/5086* (2013.01); *A61M 5/3134* (2013.01); *A61M 2005/3104* (2013.01)

(58) Field of Classification Search
CPC ........ A61M 2005/3104; A61M 5/3134; A61M 5/3202; A61M 5/347; A61M 5/5086; A61M 2025/0681; A61M 2025/09175; A61M 25/0111; A61M 25/0127; A61M 25/09041; A61M 2005/3215; A61M 5/2033;
(Continued)

(56) References Cited

U.S. PATENT DOCUMENTS 2,723,041 A   11/1955   Hart-Still
2,812,763 A   11/1957   Ferguson
(Continued)

FOREIGN PATENT DOCUMENTS

DE   3515665 C1   5/1986
DE   4318101 A1   12/1994
(Continued)

*Primary Examiner* — Brandy S Lee
(74) *Attorney, Agent, or Firm* — The Webb Law Firm

(57) ABSTRACT

A tip cap assembly adapted to close a fluid passageway of a distally projecting tip of an injection system, said tip cap assembly including an elastomeric inner cap having a frustoconical protrusion extending proximally and having a proximal face; a rigid outer cap which is securely disposed around said elastomeric inner cap; the proximal face of the frustoconical protrusion having a diameter at least greater than the diameter of the fluid passageway of the injection system.

15 Claims, 9 Drawing Sheets

(51) Int. Cl.
*A61M 5/50* (2006.01)
*A61M 5/31* (2006.01)

(58) Field of Classification Search
CPC .............. A61M 5/3204; A61M 5/3213; A61M 5/3219; A61M 2205/6072; A61M 2207/00; A61M 2209/06; A61M 35/00; A61M 2005/3103; A61M 5/31; A61B 2034/301; A61B 2034/731; A61B 34/30; A45D 2044/007; A45D 2200/155; A45D 40/30; A45D 44/002; A61H 39/02; A61N 1/303; A61N 2/002
See application file for complete search history.

(56) References Cited

U.S. PATENT DOCUMENTS

| | | | |
|---|---|---|---|
| 3,055,363 A | 9/1962 | Eckhart | |
| 3,112,747 A | 12/1963 | Cowley | |
| 3,368,557 A | 2/1968 | Hassing et al. | |
| 3,380,448 A | 4/1968 | Sadove et al. | |
| 3,381,813 A | 5/1968 | Coanda et al. | |
| 3,390,759 A | 7/1968 | Vanderbeck | |
| 3,847,183 A | 11/1974 | Meyer | |
| 3,865,236 A | 2/1975 | Rycroft | |
| 3,967,621 A | 7/1976 | Schwarz | |
| 4,240,425 A | 12/1980 | Akhavi | |
| 4,240,427 A | 12/1980 | Akhavi | |
| 4,452,473 A | 6/1984 | Ruschke | |
| 4,576,595 A | 3/1986 | Aas et al. | |
| 4,597,758 A | 7/1986 | Alto et al. | |
| 4,628,969 A | 12/1986 | Jurgens, Jr. et al. | |
| 4,636,201 A | 1/1987 | Ambrose et al. | |
| 4,718,463 A | 1/1988 | Jurgens, Jr. et al. | |
| 4,735,311 A | 4/1988 | Lowe et al. | |
| 4,753,345 A | 6/1988 | Goodsir et al. | |
| 4,765,588 A | 8/1988 | Atkinson | |
| 4,781,701 A | 11/1988 | Geprags | |
| 4,836,397 A | 6/1989 | Fowles | |
| 4,850,970 A | 7/1989 | Sutherland | |
| 4,892,222 A | 1/1990 | Schmidt et al. | |
| 4,915,704 A | 4/1990 | Miyasaka et al. | |
| 4,935,012 A | 6/1990 | Magre et al. | |
| 4,986,818 A | 1/1991 | Imbert et al. | |
| 4,991,629 A | 2/1991 | Ernesto et al. | |
| 5,009,640 A | 4/1991 | Pyret et al. | |
| 5,059,172 A | 10/1991 | Sutherland et al. | |
| 5,061,253 A | 10/1991 | Yoshida | |
| 5,069,424 A | 12/1991 | Dennany, Jr. et al. | |
| 5,088,995 A | 2/1992 | Packard et al. | |
| 5,098,400 A | 3/1992 | Crouse et al. | |
| 5,104,379 A * | 4/1992 | Nakamura | A61B 1/00062 604/111 |
| 5,125,415 A | 6/1992 | Bell | |
| 5,135,496 A * | 8/1992 | Vetter | A61M 5/34 604/111 |
| 5,167,642 A | 12/1992 | Fowles | |
| 5,184,742 A * | 2/1993 | DeCaprio | A61B 5/0215 215/356 |
| 5,224,515 A | 7/1993 | Foster et al. | |
| 5,322,518 A | 6/1994 | Schneider et al. | |
| 5,328,485 A | 7/1994 | Moreno et al. | |
| 5,373,684 A | 12/1994 | Vacca | |
| 5,395,348 A | 3/1995 | Ryan | |
| 5,437,650 A | 8/1995 | Larkin et al. | |
| 5,447,500 A | 9/1995 | Bergstresser et al. | |
| 5,509,911 A | 4/1996 | Cottone, Sr. et al. | |
| 5,531,255 A | 7/1996 | Vacca | |
| 5,531,710 A | 7/1996 | Dang et al. | |
| 5,540,666 A | 7/1996 | Barta et al. | |
| 5,554,133 A | 9/1996 | Haffner et al. | |
| 5,554,134 A | 9/1996 | Bonnichsen | |
| 5,591,143 A | 1/1997 | Trombley, III et al. | |
| 5,593,391 A | 1/1997 | Stanners | |
| 5,601,535 A | 2/1997 | Byrne et al. | |
| 5,607,400 A | 3/1997 | Thibault et al. | |
| 5,624,402 A | 4/1997 | Imbert | |
| 5,624,405 A | 4/1997 | Futagawa et al. | |
| 5,658,254 A | 8/1997 | Reichenbach et al. | |
| 5,693,025 A | 12/1997 | Stevens | |
| 5,741,236 A | 4/1998 | Kakiuti | |
| 5,755,692 A | 5/1998 | Manicom | |
| 5,807,345 A | 9/1998 | Grabenkort | |
| 5,820,604 A | 10/1998 | Fox et al. | |
| 5,820,621 A | 10/1998 | Yale et al. | |
| 5,836,919 A | 11/1998 | Skurka et al. | |
| 5,855,230 A | 1/1999 | Guala et al. | |
| 5,858,008 A | 1/1999 | Capaccio | |
| 5,989,227 A | 11/1999 | Vetter et al. | |
| 6,004,299 A | 12/1999 | Arai et al. | |
| 6,027,482 A | 2/2000 | Imbert | |
| 6,065,270 A | 5/2000 | Reinhard et al. | |
| 6,068,614 A | 5/2000 | Kimber et al. | |
| 6,190,364 B1 | 2/2001 | Imbert | |
| 6,193,696 B1 | 2/2001 | Jansen et al. | |
| 6,196,998 B1 * | 3/2001 | Jansen | A61M 5/3134 604/111 |
| 6,261,270 B1 | 7/2001 | Gault et al. | |
| 6,280,418 B1 | 8/2001 | Reinhard et al. | |
| 6,344,034 B1 | 2/2002 | Sudo et al. | |
| 6,361,524 B1 | 3/2002 | Odell et al. | |
| 6,375,022 B1 | 4/2002 | Zurcher et al. | |
| 6,394,983 B1 | 5/2002 | Mayoral et al. | |
| 6,491,665 B1 | 12/2002 | Vetter et al. | |
| 6,497,684 B2 | 12/2002 | Witowski | |
| 6,503,230 B2 | 1/2003 | Odell et al. | |
| 6,520,935 B1 | 2/2003 | Jansen et al. | |
| 6,524,282 B1 | 2/2003 | Sudo et al. | |
| 6,541,802 B2 | 4/2003 | Doyle | |
| 6,551,286 B1 | 4/2003 | Claessens | |
| 6,569,118 B2 | 5/2003 | Johnson et al. | |
| 6,585,691 B1 | 7/2003 | Vitello | |
| 6,595,964 B2 | 7/2003 | Finley et al. | |
| 6,629,957 B1 | 10/2003 | Wiklund | |
| 6,632,199 B1 | 10/2003 | Tucker et al. | |
| 6,651,956 B2 | 11/2003 | Miller | |
| 6,652,509 B1 | 11/2003 | Helgren et al. | |
| 6,662,957 B2 | 12/2003 | Zurcher et al. | |
| 6,719,732 B2 | 4/2004 | Courteix | |
| 6,802,490 B2 | 10/2004 | Leinsing et al. | |
| 6,821,267 B2 | 11/2004 | Veillon, Jr. et al. | |
| 6,840,501 B2 | 1/2005 | Doyle | |
| 7,028,927 B2 | 4/2006 | Mermet | |
| 7,104,520 B2 | 9/2006 | Leinsing et al. | |
| 7,118,560 B2 | 10/2006 | Bonaldo | |
| 7,214,214 B2 | 5/2007 | Sudo et al. | |
| 7,244,249 B2 | 7/2007 | Leinsing et al. | |
| 7,316,669 B2 | 1/2008 | Ranalletta | |
| 7,374,555 B2 | 5/2008 | Heinz et al. | |
| D581,046 S | 11/2008 | Sudo | |
| D581,049 S | 11/2008 | Sudo | |
| 7,497,843 B1 | 3/2009 | Castillo et al. | |
| 7,559,530 B2 | 7/2009 | Korogi et al. | |
| 7,563,249 B2 | 7/2009 | Schriver et al. | |
| 7,632,244 B2 * | 12/2009 | Buehler | A61M 5/50 206/726 |
| 7,635,351 B2 | 12/2009 | Peter | |
| 7,648,481 B2 | 1/2010 | Geiger et al. | |
| 7,708,951 B2 | 5/2010 | Anderson et al. | |
| 7,744,561 B2 | 6/2010 | Stamp | |
| 7,753,338 B2 | 7/2010 | Desecki | |
| 7,763,013 B2 | 7/2010 | Baldwin et al. | |
| 7,789,864 B2 | 9/2010 | Cote, Sr. et al. | |
| 7,799,010 B2 | 9/2010 | Tennican | |
| 7,803,139 B2 | 9/2010 | Fangrow, Jr. | |
| 7,803,140 B2 | 9/2010 | Fangrow, Jr. | |
| 7,806,861 B2 | 10/2010 | Witowski | |
| 7,815,614 B2 | 10/2010 | Fangrow, Jr. | |
| 7,828,777 B2 | 11/2010 | Vetter et al. | |
| D629,895 S | 12/2010 | Demleitner et al. | |
| D632,389 S | 2/2011 | Maeda et al. | |
| 7,935,091 B2 | 5/2011 | Bousquet | |
| 8,025,646 B2 | 9/2011 | Fukai et al. | |
| 8,038,182 B2 | 10/2011 | Kurimoto et al. | |

(56) References Cited

U.S. PATENT DOCUMENTS

| | | |
|---|---|---|
| 8,118,788 B2 | 2/2012 | Frezza |
| 8,167,847 B2 | 5/2012 | Anderson et al. |
| 8,172,825 B2 | 5/2012 | Solomon et al. |
| 8,231,033 B2 | 7/2012 | Webb |
| 8,231,585 B2 | 7/2012 | Heinz et al. |
| 8,231,587 B2 | 7/2012 | Solomon et al. |
| D665,498 S | 8/2012 | Tamura et al. |
| 8,235,951 B2 | 8/2012 | Hund et al. |
| 8,257,322 B2 | 9/2012 | Koehler et al. |
| 8,277,424 B2 | 10/2012 | Pan |
| 8,298,196 B1 | 10/2012 | Mansour |
| 8,328,767 B2 | 12/2012 | Solomon et al. |
| 8,348,895 B1 | 1/2013 | Vitello |
| 8,348,902 B2 | 1/2013 | Sugita et al. |
| 8,353,869 B2 | 1/2013 | Ranalletta et al. |
| 8,361,038 B2 | 1/2013 | Harding et al. |
| D675,729 S | 2/2013 | Wang |
| 8,377,010 B2 | 2/2013 | McKinnon et al. |
| D677,794 S | 3/2013 | Prpa |
| 8,403,894 B2 | 3/2013 | Lynn et al. |
| 8,475,416 B2 | 7/2013 | Lynn |
| 8,491,537 B2 | 7/2013 | Kosinski et al. |
| D688,796 S | 8/2013 | Niunoya et al. |
| D690,418 S | 9/2013 | Rosenquist |
| 8,523,830 B2 | 9/2013 | Solomon et al. |
| 8,523,831 B2 | 9/2013 | Solomon et al. |
| 8,544,665 B2 | 10/2013 | Bogle et al. |
| 8,579,870 B2 | 11/2013 | Willis et al. |
| 8,603,047 B2 | 12/2013 | Stroup |
| 8,603,048 B2 | 12/2013 | Carrez et al. |
| 8,608,723 B2 | 12/2013 | Lev et al. |
| 8,647,312 B2 | 2/2014 | Utterberg et al. |
| 8,652,109 B2 | 2/2014 | Guala |
| 8,684,206 B2 | 4/2014 | Kawachi |
| 8,708,976 B1 | 4/2014 | Yeh et al. |
| 8,715,247 B2 | 5/2014 | Mansour et al. |
| 8,721,627 B2 | 5/2014 | Alpert |
| 8,728,042 B2 | 5/2014 | Pickhard |
| 8,752,722 B2 | 6/2014 | Kuhn et al. |
| 8,757,590 B2 | 6/2014 | Naftalovitz et al. |
| 8,758,307 B2 | 6/2014 | Grimm et al. |
| 8,777,908 B2 | 7/2014 | Fangrow, Jr. |
| 8,777,909 B2 | 7/2014 | Fangrow, Jr. |
| 8,790,313 B2 | 7/2014 | Thorley |
| 8,790,330 B2 | 7/2014 | Rosenquist |
| D710,498 S | 8/2014 | Koshidaka |
| 8,801,678 B2 | 8/2014 | Panian et al. |
| 8,808,254 B2 | 8/2014 | Lynn |
| 8,832,894 B2 | 9/2014 | Rogers et al. |
| 8,840,577 B1 | 9/2014 | Zollinger et al. |
| D714,935 S | 10/2014 | Nishioka et al. |
| D717,948 S | 11/2014 | Strong et al. |
| 8,876,790 B2 | 11/2014 | Rahimy et al. |
| 8,882,719 B2 | 11/2014 | Manke et al. |
| 8,888,756 B2 | 11/2014 | Ishiwata et al. |
| 8,893,907 B2 | 11/2014 | Aneas |
| D719,650 S | 12/2014 | Arinobe et al. |
| D720,067 S | 12/2014 | Rosenquist |
| D720,452 S | 12/2014 | Jordan |
| 8,950,609 B2 | 2/2015 | Aneas |
| 8,960,242 B2 | 2/2015 | Py et al. |
| 8,961,475 B2 | 2/2015 | Solomon et al. |
| 8,974,425 B2 | 3/2015 | Tachizaki et al. |
| 8,999,471 B2 | 4/2015 | Nicola et al. |
| 9,028,451 B2 | 5/2015 | Jennings |
| D732,664 S | 6/2015 | Woehr et al. |
| D733,291 S | 6/2015 | Wang |
| D733,293 S | 6/2015 | Rogers |
| 9,079,692 B2 | 7/2015 | Solomon et al. |
| 9,604,012 B2 | 3/2017 | Horita et al. |
| 2001/0003150 A1 | 6/2001 | Imbert |
| 2001/0045539 A1 | 11/2001 | Doyle |
| 2002/0013556 A1 | 1/2002 | Cote, Sr. et al. |
| 2002/0133124 A1 | 9/2002 | Leinsing et al. |
| 2003/0094429 A1 | 5/2003 | Sudo et al. |
| 2003/0209681 A1 | 11/2003 | Leinsing et al. |
| 2004/0039341 A1 | 2/2004 | Ranalletta |
| 2004/0116858 A1 | 6/2004 | Heinz et al. |
| 2004/0116869 A1 | 6/2004 | Heinz et al. |
| 2004/0153038 A1 | 8/2004 | Guala |
| 2004/0171993 A1 | 9/2004 | Bonaldo |
| 2004/0215148 A1 | 10/2004 | Hwang et al. |
| 2005/0063857 A1 | 3/2005 | Alheidt et al. |
| 2005/0075611 A1 | 4/2005 | Hetzler et al. |
| 2005/0159710 A1 | 7/2005 | Utterberg |
| 2006/0129109 A1 | 6/2006 | Shaw et al. |
| 2006/0178627 A1 | 8/2006 | Geiger et al. |
| 2006/0211996 A1 | 9/2006 | Trinchera et al. |
| 2006/0264848 A1 | 11/2006 | Fangrow |
| 2007/0088292 A1 | 4/2007 | Fangrow, Jr. |
| 2007/0088293 A1 | 4/2007 | Fangrow, Jr. |
| 2007/0088294 A1 | 4/2007 | Fangrow, Jr. |
| 2007/0287965 A1 | 12/2007 | Strong et al. |
| 2008/0097310 A1 | 4/2008 | Buehler et al. |
| 2008/0125714 A1 | 5/2008 | Cude |
| 2008/0132851 A1 | 6/2008 | Shaw et al. |
| 2008/0249479 A1 | 10/2008 | Zinger et al. |
| 2009/0012426 A1 | 1/2009 | Tennican |
| 2009/0069757 A1 | 3/2009 | Muri et al. |
| 2009/0082725 A1 | 3/2009 | Witowski |
| 2009/0149816 A1 | 6/2009 | Hetzler et al. |
| 2009/0171322 A1 | 7/2009 | Kurimoto et al. |
| 2009/0177170 A1 | 7/2009 | Kitani et al. |
| 2009/0283493 A1 | 11/2009 | Witowski |
| 2009/0287160 A1 | 11/2009 | Sudo et al. |
| 2010/0030163 A1 | 2/2010 | Carrez et al. |
| 2010/0030164 A1 | 2/2010 | Kimball et al. |
| 2010/0198163 A1 | 8/2010 | Bonnet |
| 2010/0256573 A1 | 10/2010 | Mansour et al. |
| 2010/0256574 A1 | 10/2010 | Simpson et al. |
| 2010/0331787 A1 | 12/2010 | Fournie |
| 2011/0015578 A1 | 1/2011 | Lowke |
| 2011/0046572 A1 | 2/2011 | Fangrow |
| 2011/0095528 A1 | 4/2011 | Forberg |
| 2011/0184382 A1 | 7/2011 | Cady |
| 2011/0217212 A1* | 9/2011 | Solomon ............ A61M 39/165 422/292 |
| 2011/0257607 A1 | 10/2011 | Whitley |
| 2011/0288505 A1 | 11/2011 | Weibel |
| 2011/0301546 A1 | 12/2011 | Harms et al. |
| 2011/0301552 A1 | 12/2011 | Nakanishi et al. |
| 2012/0109059 A1 | 5/2012 | Ranalletta et al. |
| 2012/0302997 A1 | 11/2012 | Gardner et al. |
| 2013/0006189 A1 | 1/2013 | Tsals et al. |
| 2013/0012886 A1 | 1/2013 | Kawachi |
| 2013/0035643 A1 | 2/2013 | Kawamura |
| 2013/0035667 A1 | 2/2013 | Anderson et al. |
| 2013/0085466 A1 | 4/2013 | Ishiwata et al. |
| 2013/0090610 A1 | 4/2013 | Stout et al. |
| 2013/0150795 A1 | 6/2013 | Snow |
| 2013/0165851 A1 | 6/2013 | Geiger et al. |
| 2013/0165867 A1 | 6/2013 | Isaacson et al. |
| 2013/0165868 A1 | 6/2013 | Isaacson et al. |
| 2013/0190684 A1 | 7/2013 | Panian et al. |
| 2013/0197453 A1 | 8/2013 | Yeh |
| 2013/0197485 A1 | 8/2013 | Gardner et al. |
| 2013/0221015 A1 | 8/2013 | Schmidt et al. |
| 2013/0226099 A1 | 8/2013 | Fangrow |
| 2013/0231616 A1 | 9/2013 | Fangrow et al. |
| 2013/0237911 A1 | 9/2013 | Von Schuckmann |
| 2013/0245531 A1 | 9/2013 | Brandl et al. |
| 2013/0261562 A1 | 10/2013 | Fabian et al. |
| 2013/0296791 A1 | 11/2013 | Segev et al. |
| 2013/0304026 A1 | 11/2013 | Luther et al. |
| 2013/0310764 A1 | 11/2013 | Burkholz et al. |
| 2013/0338588 A1 | 12/2013 | Grimm et al. |
| 2013/0338604 A1 | 12/2013 | Roedle |
| 2014/0005612 A1 | 1/2014 | Guala |
| 2014/0025017 A1 | 1/2014 | Horita et al. |
| 2014/0058336 A1 | 2/2014 | Burkholz et al. |
| 2014/0135696 A1 | 5/2014 | Ruan et al. |
| 2014/0142513 A1 | 5/2014 | Bonnet |
| 2014/0142519 A1 | 5/2014 | Truitt et al. |
| 2014/0180219 A1 | 6/2014 | Ho et al. |

(56) References Cited

U.S. PATENT DOCUMENTS

| | | |
|---|---|---|
| 2014/0228777 A1 | 8/2014 | Simpson et al. |
| 2014/0249476 A1 | 9/2014 | Grimm et al. |
| 2014/0249477 A1 | 9/2014 | Grimm et al. |
| 2014/0249486 A1 | 9/2014 | Grimm et al. |
| 2014/0261558 A1 | 9/2014 | Rogers et al. |
| 2014/0276459 A1 | 9/2014 | Yeh et al. |
| 2014/0276460 A1 | 9/2014 | Zollinger et al. |
| 2014/0276461 A1 | 9/2014 | Zollinger et al. |
| 2014/0316350 A1 | 10/2014 | Yamaguchi et al. |
| 2014/0346134 A1 | 11/2014 | Tixier |
| 2014/0358078 A1 | 12/2014 | Fischer et al. |
| 2014/0371686 A1 | 12/2014 | Sano et al. |
| 2015/0045746 A1 | 2/2015 | Macy, Jr. et al. |
| 2015/0126942 A1 | 5/2015 | Lopez et al. |
| 2015/0141937 A1 | 5/2015 | Bonaldo |
| 2015/0148756 A1 | 5/2015 | Lynn |
| 2015/0157846 A1 | 6/2015 | Fangrow, Jr. |
| 2015/0165127 A1 | 6/2015 | Haefele et al. |
| 2015/0182962 A1 | 7/2015 | Quarre et al. |
| 2015/0217061 A1 | 8/2015 | Sadowski et al. |
| 2015/0231384 A1 | 8/2015 | Ma et al. |
| 2015/0238703 A1 | 8/2015 | Glocker |
| 2015/0246185 A1 | 9/2015 | Heinz |
| 2015/0265827 A1 | 9/2015 | Keyser et al. |
| 2015/0265839 A1 | 9/2015 | Pertijs et al. |
| 2015/0283329 A1 | 10/2015 | Shaw et al. |
| 2015/0283373 A1 | 10/2015 | Yeh et al. |

FOREIGN PATENT DOCUMENTS

| | | |
|---|---|---|
| DE | 4434644 A1 | 4/1996 |
| DE | 19547431 A1 | 6/1997 |
| DE | 19956243 A1 | 5/2000 |
| DE | 19909824 A1 | 9/2000 |
| DE | 10127779 A1 | 12/2002 |
| DE | 102011120637 A2 | 6/2013 |
| EP | 0098411 A2 | 1/1984 |
| EP | 0136272 A1 | 4/1985 |
| EP | 0634183 A1 | 1/1995 |
| EP | 0707859 A1 | 4/1996 |
| EP | 0716860 A2 | 6/1996 |
| EP | 0720857 A1 | 7/1996 |
| EP | 0856332 A1 | 8/1998 |
| EP | 0974372 A1 | 1/2000 |
| EP | 1080742 A1 | 3/2001 |
| EP | 1192965 A1 | 4/2002 |
| EP | 1378223 A1 | 1/2004 |
| EP | 1600190 A1 | 11/2005 |
| EP | 1779882 A2 | 5/2007 |
| EP | 1923086 A1 | 5/2008 |
| EP | 2092948 A1 | 8/2009 |
| EP | 2138202 A1 | 12/2009 |
| EP | 2253349 A1 | 11/2010 |
| EP | 2262560 A1 | 12/2010 |
| EP | 2266646 A1 | 12/2010 |
| EP | 2332601 A1 | 6/2011 |
| EP | 2554203 A1 | 2/2013 |
| EP | 2823842 A1 | 1/2015 |
| GB | 2249727 A | 5/1992 |
| GB | 2379253 A | 3/2003 |
| JP | H07250894 A | 10/1995 |
| JP | H08215307 A | 8/1996 |
| JP | 2000254226 A | 9/2000 |
| JP | 2002153539 A | 5/2002 |
| JP | 2003054615 A | 2/2003 |
| JP | 2004160206 A | 6/2004 |
| JP | 2004527361 A | 9/2004 |
| JP | 2005110873 A | 4/2005 |
| JP | 2007111156 A | 5/2007 |
| JP | 2009219855 A | 10/2009 |
| JP | 2009240684 A | 10/2009 |
| JP | 2010131064 A | 6/2010 |
| JP | 4522071 B2 | 8/2010 |
| JP | 2011230839 A | 11/2011 |
| JP | 2013078442 A | 5/2013 |
| WO | 9625964 A1 | 8/1996 |
| WO | 02056958 A2 | 7/2002 |
| WO | 03076001 A2 | 9/2003 |
| WO | 03076002 A1 | 9/2003 |
| WO | 2005023343 A1 | 3/2005 |
| WO | 2005032627 A1 | 4/2005 |
| WO | 2007146921 A2 | 12/2007 |
| WO | 2008010958 A2 | 1/2008 |
| WO | 2009063313 A2 | 5/2009 |
| WO | 2009109312 A1 | 9/2009 |
| WO | 2009123150 A1 | 10/2009 |
| WO | 2010034356 A1 | 4/2010 |
| WO | 2010084006 A1 | 7/2010 |
| WO | 2010119271 A1 | 10/2010 |
| WO | 2010124676 A1 | 11/2010 |
| WO | 2011125475 A1 | 10/2011 |
| WO | 2012061478 A2 | 5/2012 |
| WO | 2012144026 A1 | 10/2012 |
| WO | 2013047042 A1 | 4/2013 |
| WO | 2015055608 A1 | 4/2015 |

\* cited by examiner

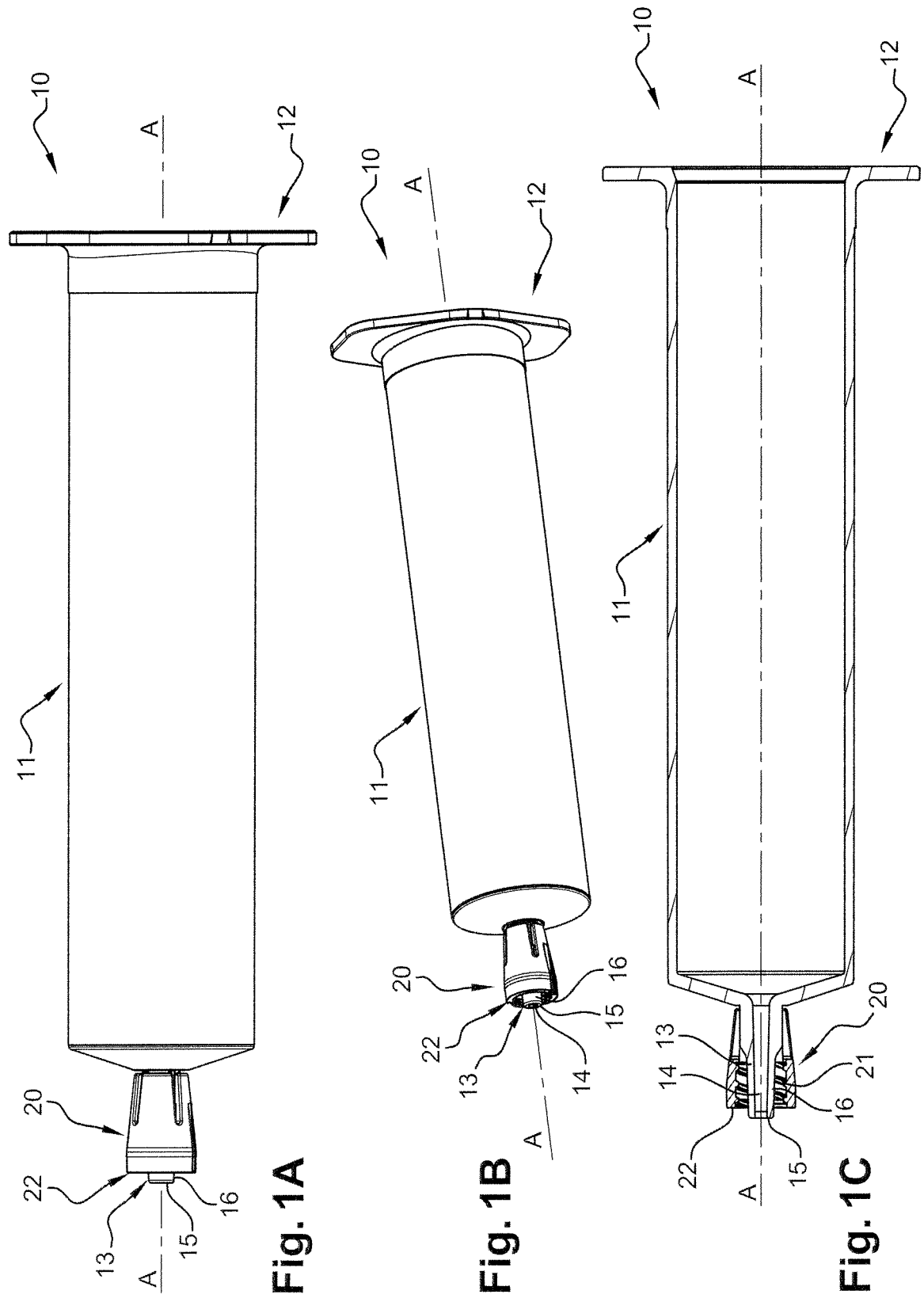

TIP CAP ASSEMBLY FOR CLOSING AN INJECTION SYSTEM

CROSS-REFERENCE TO RELATED APPLICATIONS

This application is the United States national phase of International Application No. PCT/EP2014/071950 filed Oct. 14, 2014, and claims priority to European Patent Application No. 13306414.7 filed Oct. 15, 2013, the disclosures of which are hereby incorporated in their entirety by reference.

BACKGROUND OF THE INVENTION

Field of the Invention

The present invention generally relates to an injection system such as a syringe, as well as a tip cap assembly for securely closing the distal tip of the injection system.

Description of Related Art

In this application, the distal end of a component or apparatus must be understood as meaning the end furthest from the hand of the user and the proximal end must be understood as meaning the end closest to the hand of the user, with reference to the injection system intended to be used with said component or apparatus. As such, in this application, the distal direction must be understood as the direction of injection with reference to the injection system, and the proximal direction is the opposite direction, i.e. the direction towards the hand of the user.

Current medicine uses a wide range of injection systems to deliver fluids into the body of patients. For example, such injection systems may include auto-injectors, medical pens or syringes. Conventional syringes are widely used because of their common availability, ease of use and limited cost. They usually comprise a longitudinal barrel with an open proximal end and a substantially closed distal end including a distally projecting tip. The fluid intended to be injected can be stored into the syringe barrel, and in this case, the open proximal end is closed by a stopper in sliding fluid-tight engagement within the barrel and actuated by a plunger rod. The tip is provided with a fluid passageway extending therethrough to allow the injection of the fluid when a distal pressure is applied on the plunger. The tip can be provided with an attached needle or can be of a luer type, meaning needle-free. Syringe barrels are typically made of glass or plastic. Glass is preferably chosen for its chemical neutrality and low gas permeability whereas plastic is preferably chosen for its resistance to shocks.

Almost all fluids can be injected with a syringe. For example, a fluid can be a pharmaceutical solution such as a drug, a vaccine, vitamins or dietary minerals. Syringes are also useful to inject diagnostic solutions, cosmetic fluids, including gels such as hyaluronic acid or silicone compositions. The injection can be performed in every part of the body including skin, hypodermis, muscle and veins, depending on the application.

Usually, syringes are provided empty and filled with a fluid immediately before the injection, but now syringes are more and more provided prefilled with the fluid to inject, ready to be used, leading to several advantages. First of all, prefilled syringes reduce the number of steps required to perform an injection, which is particularly valuable in emergency medicine. Furthermore, prefilled syringes reduce the risk of human error on the quantity or the quality of the fluid to be injected. Indeed, the administration of a wrong dose or undesired medicine may impede medical treatments efficacy and cause death or severe injuries on treated patients. Additionally, prefilled syringes reduce the risk of contamination linked with the transfer of fluids from multidose vials into empty syringes, such contamination also leading to impede medical treatments efficacy. Finally, prefilled syringes are particularly useful to store fluids which are difficult to transfer. For example, it is appropriate to use such syringes when viscous liquids or gels are employed for cosmetic applications, or when pharmaceutical compositions are employed for anesthetic applications.

During the time between the filling of the syringe and its use, needle-free syringes are equipped with a tip cap to close the distally extending tip. Indeed, as fluids are stored in the prefilled syringe for an extended period of time, typically from 6 to 18 months before injection, the injection system must be kept perfectly sealed during this period. The quality of the sealing between the tip cap and the syringe is very important as a deficient sealing could damage the nature or the purity of the fluids, leading to wastage of valuable fluids, potential unacceptable risks for the patients and potential unacceptable risks for the medical staff according to the nature of the pharmaceutical compositions stored inside the syringes.

Moreover, the syringe should be opened easily when required and the tip cap should be removed without excessive effort. But it is well known that sticking phenomenon can occur when a tip cap is plugged on the tip of a syringe. Indeed, it has been observed that when two materials are compressed together over an extended period of time, such phenomenon of sticking could occur and prevent a fast and easy opening of a prefilled syringe. Consequently, a tip cap difficult to open would lead to the rejection of the prefilled syringes before use and would constitute an unacceptable economic loss. This could also lead to the death or severe injury of patients requiring an immediate injection.

Finally, the outside surface of the syringe tip needs to be preserved from contaminants, such as dust or micro-organisms, which could migrate from the tip to the fluid passageway. Indeed, if these contaminants are injected with the pharmaceutical fluid to a patient, it would trigger an inappropriate immune response, lessen the treatment efficacy and decrease the patient's trust into his treatment.

SUMMARY OF THE INVENTION

Therefore, it is an object of the invention to provide a tip cap ensuring an improved and sustainable sealing of the syringe tip. It is further an object of the invention to provide a tip cap that can be easily unplugged from the syringe tip. It is another object of the invention to maintain the syringe tip sterility during storage.

A first aspect of the invention is a tip cap assembly adapted to close the fluid passageway of a distally projecting tip of an injection system, said tip cap assembly including:
- an elastomeric inner cap having a frustoconical protrusion extending proximally, said frustoconical protrusion having a proximal face, and
- a rigid outer cap which is or can be securely disposed around said elastomeric inner cap, the proximal face of the frustoconical protrusion having a diameter at least greater than the diameter of the fluid passageway of the injection system.

Due to the frustoconical protrusion of the elastomeric inner cap, the contact between said elastomeric inner cap and the distally projecting tip is limited to the small distal surface of said tip. Indeed, the proximal face of the elastomeric inner cap is essentially perpendicular to the rotational axis of the cone from which the frustoconical protrusion is derived. The surface of the proximal face may be flat or may show a slight curvature radius, the center of which being situated on said rotational axis. Moreover, the diameter of the proximal face of the frustoconical protrusion of the elastomeric inner cap at least greater than the diameter of the fluid passageway does not allow the frustoconical protrusion to penetrate the fluid passageway of the distally projecting tip. This significantly reduces or cancels the sticking phenomenon that may happen after an extended period of storage and therefore allows a quick and easy removal of the tip cap assembly from the injection system. The proximal face of the frustoconical protrusion may be the most proximal face of the elastomeric inner cap.

For example, the elastomeric inner cap has globally the shape of a cylinder and the rigid outer cap has a globally tubular shape provided with a distal transversal wall. For example, the elastomeric inner cap is received within the rigid outer cap so that the outer wall of the elastomeric inner cap is at least partially in contact with the inner wall of the rigid outer cap, in particular with the inner wall of a tubular part of the rigid outer cap. The elastomeric inner cap may be received with friction within the rigid outer cap.

Due to its elastomeric nature, the elastomeric inner cap has the capability of being deformed when it is submitted to pressure, for example when a distal pressure is applied. For example, when the elastomeric inner cap has the global shape of a cylinder, it may be deformed radially outwardly under the effect of a longitudinal pressure, for example a distal pressure or a proximal pressure.

In aspects of the disclosure, the tip cap assembly is provided with stress-limiting means, also referred to as a stress-limiting element, allowing said elastomeric inner cap to be substantially deformed when the assembly closes said passageway, for example when a distal pressure is exerted on the elastomeric inner cap by the syringe tip. In particular, the stress-limiting means allow at least part of the elastomeric inner cap to be deformed radially outwardly, although the elastomeric inner cap is received within the rigid outer cap. The deformation of the elastomeric inner cap ensures an optimal sealing of the fluid passageway and the syringe tip. However, the rigid outer cap could be deformed by the stress transmitted by the elastomeric inner cap over an extended period of storage, and such deformed rigid cap might lead to a deficient sealing. The stress-limiting means avoids the unintended deformation of the rigid outer cap by limiting the amount of stress transmitted to the rigid outer cap by the deformation of the elastomeric inner cap when it closes said passageway, for example when distal pressure is exerted on the elastomeric inner cap, and contributes to maintain the optimal sealing over an extended period of time.

In aspects of the disclosure, these stress-limiting means include at least one window and more preferably two diametrically opposed longitudinal windows provided onto said rigid outer cap. For example, the window(s) are provided on a tubular wall of the rigid outer cap. These windows accommodate the elastomeric material from the elastomeric inner cap resulting from the deformation caused by both the closing of the passageway and the insertion of the elastomeric cap into the rigid outer cap, for example when the diameter of the elastomeric cap is greater than the internal diameter of the rigid cap. In particular, the windows allow the elastomeric inner cap to be deformed radially outwardly. In particular, when located on a tubular wall of the rigid outer cap, the window(s) may receive some part of the elastomeric inner cap which is deformed radially outwardly.

In aspects, these stress-limiting means further include a distal opening provided into said rigid outer cap to accommodate the distal deformation of the elastomeric inner cap when the tip cap assembly closes said the fluid passageway, for example when the elastomeric inner cap is submitted to distal pressure. The distal opening may be provided in the distal transversal wall of the rigid outer cap.

In aspects of the disclosure, the elastomeric cap and the outer rigid cap include holding means, also referred to as a holding element, intended to secure said elastomeric inner cap into said rigid outer cap.

In aspects of the disclosure, said holding means include a shoulder provided into the rigid outer cap and a radial rim provided onto the elastomeric inner cap, the elastomeric inner cap being proximally blocked by the contact between the distal rim and said shoulder. The shoulder and the radial rim therefore form proximal blocking means, also referred to as a proximal blocking element, for blocking the proximal movement of the elastomeric inner cap with respect to the rigid outer cap.

In aspects of the disclosure, said holding means further include at least one abutment surface provided into the rigid outer cap, and a distal face provided onto the elastomeric inner cap, said elastomeric inner cap being distally blocked by the contact between the abutment surface and the distal face. The abutment surface and the distal face therefore form distal blocking means, also referred to as a distal blocking element, for blocking the distal movement of the elastomeric inner cap with respect to the rigid outer cap.

The shoulder, the radial rim, the abutment surface and the distal face form altogether locking means, also referred to as a locking arrangement, both in proximal and in distal translation of the elastomeric inner cap with respect to the rigid outer cap.

In aspects of the disclosure, the length L1 defined between an abutment surface and the shoulder of the rigid outer cap is greater than the length L2 defined between the distal face and the radial rim of said elastomeric inner cap, L1 and L2 being measured along a longitudinal axis of the tip cap assembly. A gap is therefore left between the rigid outer cap and the elastomeric inner cap: the presence of such a gap simplifies the assembling of the tip cap assembly and allows an optimal and sustainable closure, even with non-standard syringes.

A second aspect of the disclosure is an injection system including a longitudinal barrel, a distally projecting tip provided with a fluid passageway extending therethrough, a distal surface and a lateral surface, where the injection system further includes a tip cap assembly according to the first aspect of the disclosure.

A third aspect of the disclosure is an injection system including a longitudinal barrel having a distally projecting tip and a tip cap assembly, said distally projecting tip being provided with a fluid passageway extending therethrough, a distal surface and a lateral surface, said tip cap assembly including an elastomeric inner cap including a frustoconical protrusion and a rigid outer cap which can be securely disposed around said elastomeric inner cap, said assembly being configured so that, when said tip cap assembly closes said passageway, said frustoconical protrusion contacts said distally projecting tip only at the distal surface.

In aspects of the disclosure, the rigid outer cap is provided with a sterility skirt intended for a circumferential sealing of the lateral surface of said distally projecting tip when said assembly closes said fluid passageway. This sterility skirt maintains sterile the distal tip of the syringe during storage and thus the content of the injection system.

In aspects of the disclosure, the sterility skirt is further provided with at least one annular ridge. For example, the annular ridge is provided on the inner wall of the sterility skirt. The at least one annular ridge may enhance the sealing provided between the sterility skirt and the lateral surface of the distally projecting tip.

In aspects of the disclosure, the injection system is provided with a collar securely engaged around said distal tip, having an inner thread and a distal rim, and wherein said rigid outer cap is provided with an outer thread able to cooperate with the thread of the collar to close said passageway.

In aspects of the disclosure, the rigid outer cap is provided with a proximal abutment surface contacting the distal rim of the collar when said tip cap assembly closes said passageway.

A fourth aspect of the disclosure is a tip cap assembly adapted to close the fluid passageway of the distally projecting tip of an injection system. The tip cap assembly includes an elastomeric inner cap having a distal portion and a proximal portion and a rigid outer cap adapted to be securely disposed around the elastomeric inner cap. The proximal portion of the elastomeric inner cap includes a frustoconical protrusion and a proximal face having a diameter greater than the diameter of the fluid passageway of the injection system.

In aspects of the disclosure, the tip cap assembly further includes a stress-limiting means to accommodate deformation of the elastomeric inner cap when the assembly closes the fluid passageway. The stress-limiting means may include at least one window in the rigid outer cap and, preferably, two diametrically opposed longitudinal windows. Alternatively or in addition, the stress-limiting means may include a distal opening in the rigid outer cap.

In aspects of the disclosure, the elastomeric cap and the outer rigid cap each include at least one engagement surface, wherein contact of the engagement surface of the elastomeric inner cap with the engagement surface of the rigid outer cap secures the elastomeric inner cap to the rigid outer cap. The engagement surface of the rigid outer cap may include a shoulder, and the engagement surface of the elastomeric inner cap may include a radial rim, wherein the radial rim contacts the shoulder at least when a proximal pressure is applied to the elastomeric inner cap. Alternatively or in addition, the engagement surface of the rigid outer cap may include at least one abutment surface, and the engagement surface of the elastomeric inner cap may include a distal face, wherein the at least one abutment surface contacts the distal face at least when a distal pressure is applied to the elastomeric inner cap. In the aspect where the rigid outer cap includes a first engagement surface including a shoulder and a second engagement surface including an abutment surface and the elastomeric inner cap includes a first engagement surface including a radial rim and a second engagement surface including distal face, the length L1 defined between the abutment surface and the shoulder of the rigid outer cap may be greater than the length L2 defined between the distal face and the radial rim of the elastomeric inner cap.

In aspects of the disclosure, the outer rigid cap may include a distal portion, a central portion, and a proximal portion. The at least one stress-limiting means, preferably a longitudinal window, may be located in the distal portion of the outer rigid cap and the proximal section may have a frustoconical shape. The outer rigid cap may further include internal and/or external reinforcement means, also referred to as reinforcement elements. The reinforcement means may be longitudinal or circumferential ribs.

In aspects of the disclosure, the elastomeric inner cap may include a distal portion and a proximal portion. The distal portion may be essentially cylindrical with a flat distal face and the proximal portion may comprise a frustoconical protrusion. The diameter of the proximal portion may be less than the diameter of the distal portion. The proximal portion of the elastomeric inner cap may also include a circular bump.

In aspects of the disclosure, the elastomeric cap may adopt three different configurations: a free configuration when it is not assembled with the rigid cap, a first stressed configuration when it is assembled into the rigid cap to form the tip cap assembly and a second stressed configuration due to the distal pressure applied by the distally projecting tip when the tip cap assembly closes the fluid passageway of an injection system.

In the second stressed configuration, the distal end of the elastomeric inner cap is received in the distal portion of the outer rigid cap and the proximal portion of the elastomeric inner cap is received in the central portion of the outer rigid cap. The outside diameter of the distal portion of the elastomeric inner cap may be greater than the inside diameter of the distal portion of the outer rigid cap and/or the outside diameter of the proximal portion of the elastomeric inner cap may be greater than the inside diameter of the central portion of the outer rigid cap in order to enhance contact between the engagement surfaces of the outer rigid cap and the elastomeric inner cap.

In the third stressed configuration, the elastomeric inner cap is further compressed between the rigid inner cap and the distally projecting tip of the injection system.

In both the second and the third stressed conditions, the stress-limiting means acts to reduce the stress placed on the rigid outer cap due to the compression of the elastomeric inner cap.

A fifth aspect of the disclosure is an injection system including a longitudinal barrel, and a distally projecting tip having a fluid passageway extending therethrough, a distal surface, and a lateral surface, wherein the injection system further includes a tip cap assembly as described above.

In aspects of the disclosure, when the tip cap assembly closes the fluid passageway, the frustoconical protrusion only contacts the distal surface of the distally projecting tip.

In aspects of the disclosure, the rigid outer cap may further include a sterility skirt that provides a circumferential seal between the lateral surface of the distally projecting tip and the rigid outer cap when the tip cap assembly closes the passageway. The sterility skirt may include at least one annular ridge.

In aspects of the disclosure, the injection system may further include a collar securely engaged around the distal tip. The collar may have an inner thread and a distal rim. In this aspect, the rigid outer cap includes an outer thread adapted to cooperate with the inner thread of the collar in order to close the passageway. The rigid outer cap may further include a proximal abutment surface that contacts the distal rim of the collar when the tip cap assembly closes the passageway. This engagement of the proximal abutment surface and the distal rim of the collar prevents rotational movement of the tip with respect to the injection system to avoid damage to the tip cap assembly and assures correct positioning of the tip cap with regard to the collar to signal the user that a seal has been formed.

A sixth aspect of the disclosure is an injection system including a longitudinal barrel, a distally projecting tip and a collar provided with an inner thread. The collar is securely engaged around the distally projecting tip and the distally projecting tip has a lateral surface and a fluid passageway extending therethrough. The injection system further includes a tip-cap assembly including an elastomeric inner cap and a rigid outer cap that is or can be securely disposed around the elastomeric inner cap. The rigid outer cap of the tip cap assembly includes an outer thread intended to be screwed with the inner thread of the collar, a frustoconical extension and a radial recess between the outer thread and the frustoconical extension. The frustoconical extension is intended to ensure a circumferential sealing of the distally projecting tip around the lateral surface in order to act as a sterility skirt when the tip-cap assembly closes the passageway of the projecting tip.

In aspects of the disclosure, the frustoconical extension of the rigid outer cap may be provided with at least one annular ridge, preferably three.

A seventh aspect of the disclosure is a tip-cap assembly adapted to close the fluid passageway of the distally projecting tip of an injection system. The tip-cap assembly includes an elastomeric inner cap which has a distal face and a radial rim, and a length L2 defined as the distance between the distal face and the radial rim. The tip-cap assembly further includes a rigid outer cap which is or can be securely disposed around the elastomeric inner cap, with a shoulder and at least one abutment surface, and a length L1 defined as the distance between the at least one abutment surface and the shoulder. The elastomeric inner cap is distally blocked by the contact between the distal face and the at least one abutment surface, and proximally blocked by the contact between the radial rim and the shoulder. The length L1 is greater than the length L2 in order to allow a limited translation of the elastomeric inner cap within the rigid outer cap.

BRIEF DESCRIPTION OF THE DRAWINGS

The present invention will now be described in greater detail based on the following description and the appended drawings, in which:

FIG. 1A is a side view of a syringe without a tip cap

FIG. 1B is a perspective view of a syringe without a tip cap;

FIG. 1C is a cross-section view of a syringe without a tip cap;

DETAILED DESCRIPTION OF THE DISCLOSURE

Figure 2A:
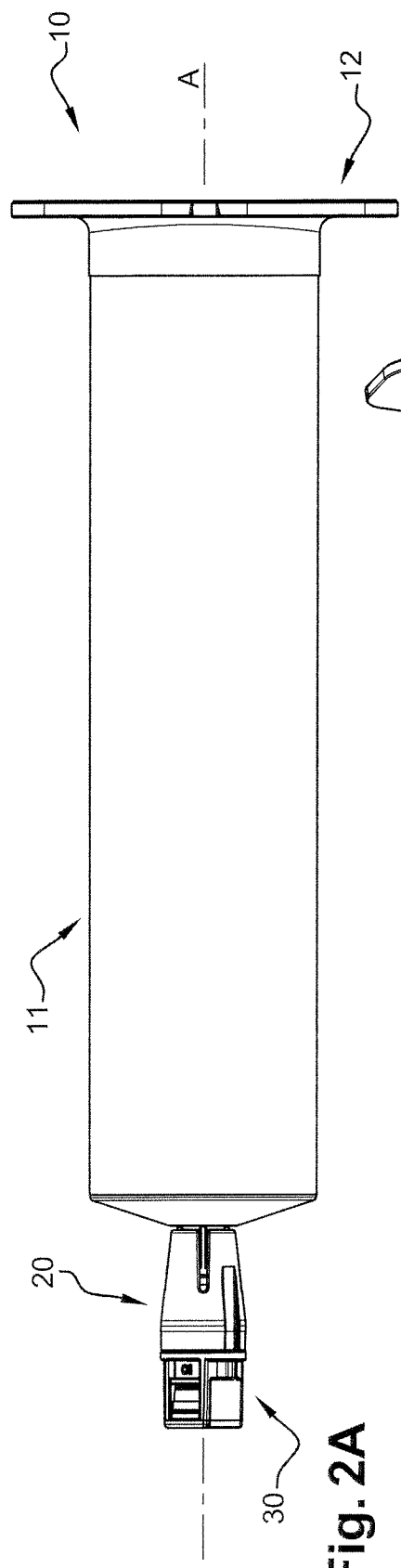
FIG. 2A is a side view of the syringe of FIGS. 1A-1C closed by a tip cap assembly of an abstract of the present disclosure.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures.

FIGS. 1A-1C show an injection system 10 in the form of a luer syringe according to an aspect of the disclosure. The present disclosure could be used with any other types of injection systems, such as a pen, or an infusion system, provided they include a distally projecting tip. For sake of clarity, the present disclosure will only be described with a luer syringe 10. The syringe 10 includes a longitudinal barrel 11 having a longitudinal axis A, a proximal flange 12 and a distally projecting tip 13. The distally projecting tip 13 includes a fluid passageway 14 extending therethrough, a distal surface 15 and a lateral surface 16 (see FIG. 1C) which is substantially tubular. A collar 20 is securely engaged around the tip 13, for example by clipping, screwing or welding. In another aspect (not shown), the collar 20 is molded with the longitudinal barrel with which it forms only one part. The collar 20 is provided with an inner thread 21 and a distal rim 22. The syringe 10 is further provided with a stopper and a plunger rod, not shown in FIGS. 1A-1C.

Figure 2B:
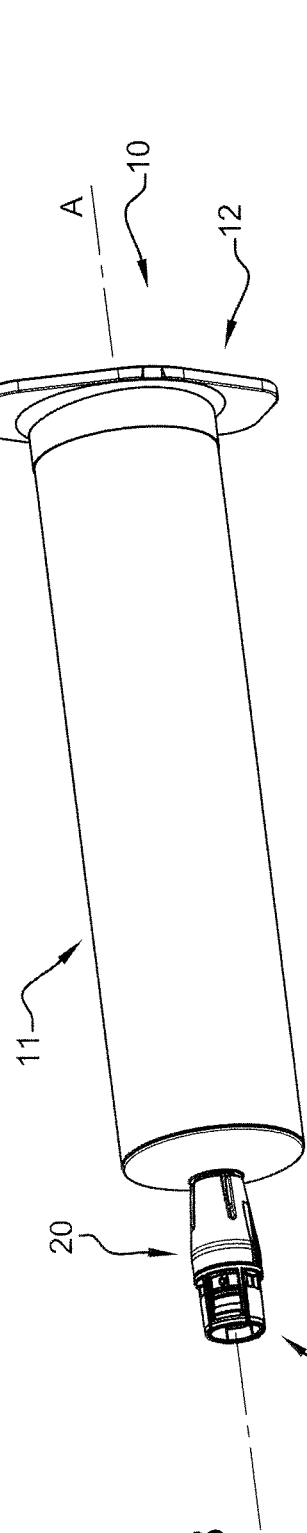
FIG. 2B is a perspective view of the syringe of FIGS. 1A-1C closed by a tip cap assembly of an aspect of the present disclosure.
Figure 2C:
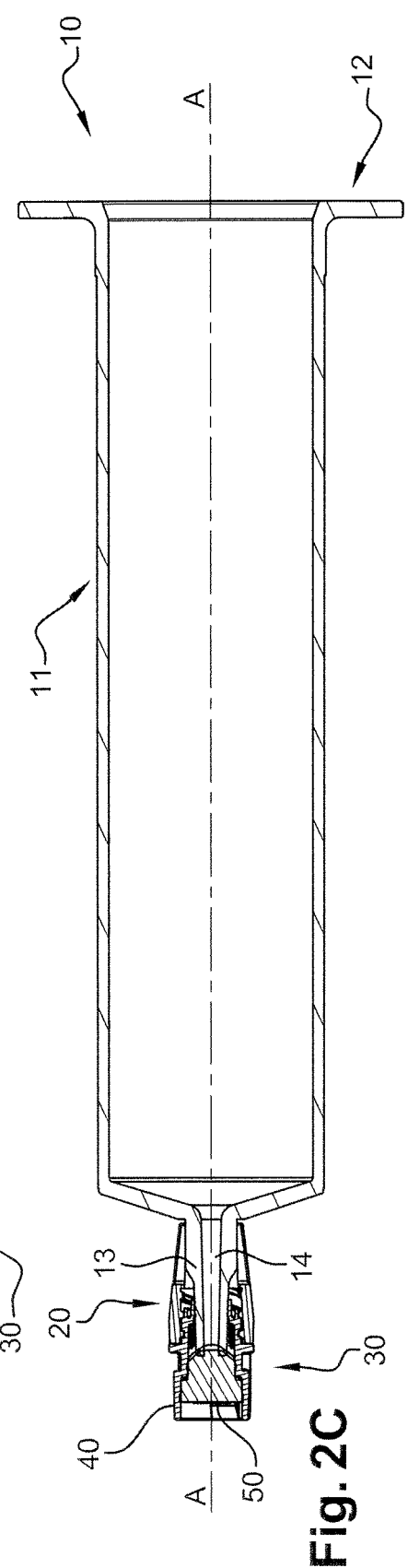
FIG. 2C is a cross-section view of the syringe of FIGS. 1A-1C closed by a tip cap assembly of an aspect of the present disclosure.
Figure 3A:
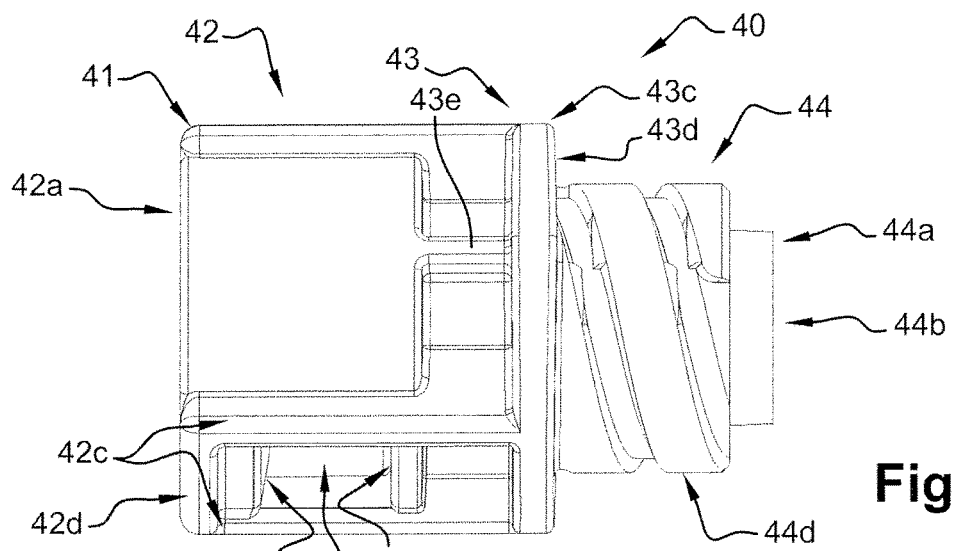
FIG. 3A is a side view of the rigid outer cap of the tip cap assembly of FIGS. 2A and 2B.
Figure 3B:
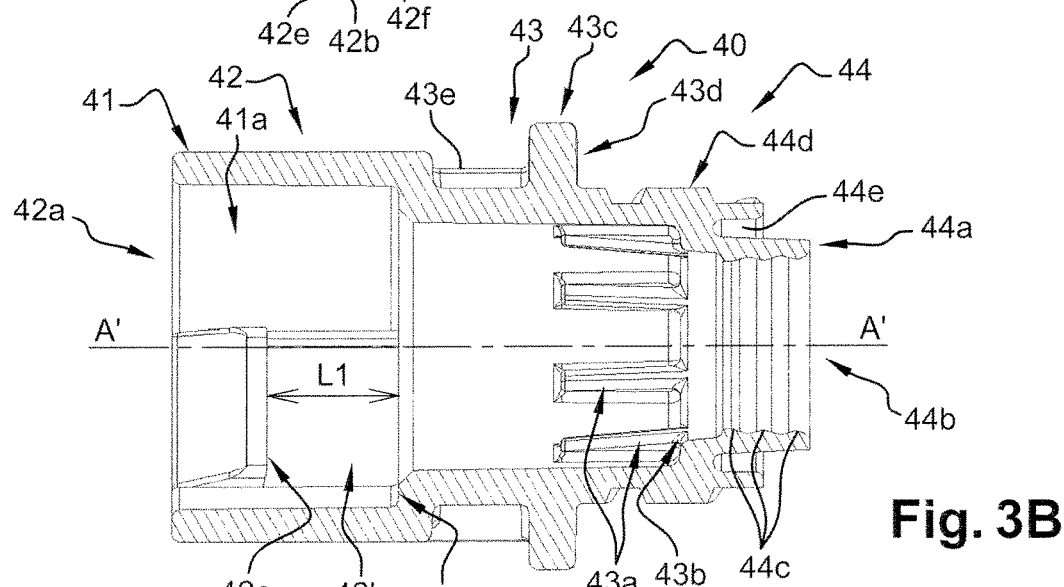
FIG. 3B is a cross-section view of the rigid outer cap of the tip cap assembly of FIGS. 2A and 2B.
Figure 3C:
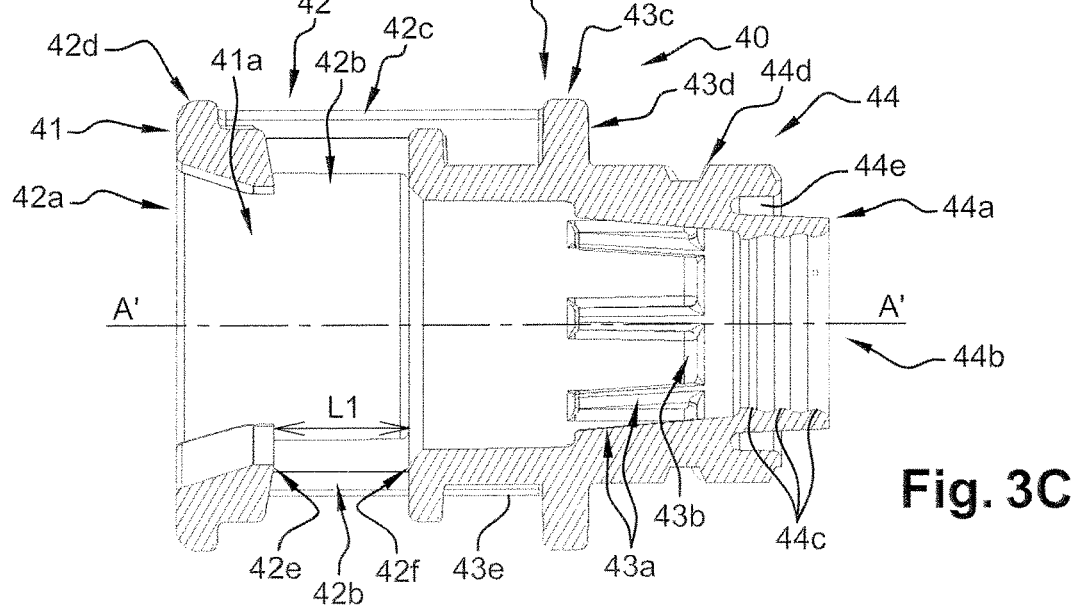
FIG. 3C is another cross-section view of the rigid outer cap of the tip cap assembly of FIGS. 2A and 2B.
Figure 3D:
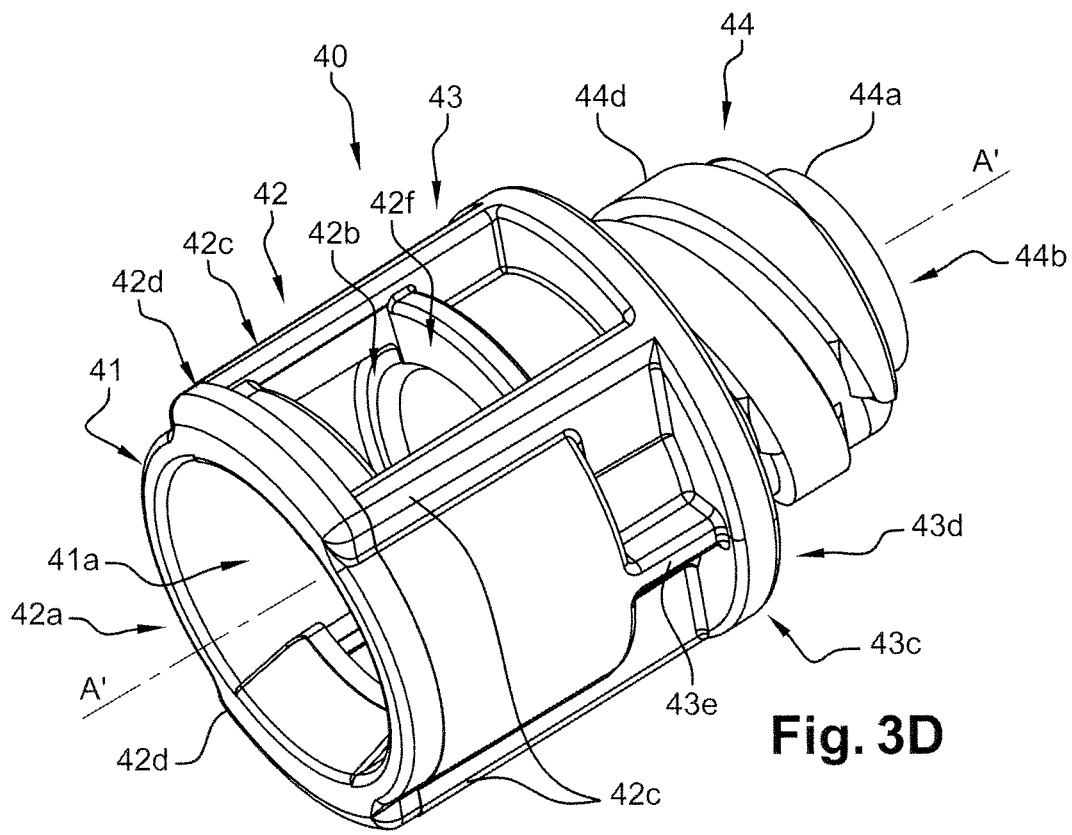
FIG. 3D is a perspective view of the rigid outer cap of the tip cap assembly of FIGS. 2A and 2B.
Figure 3E:
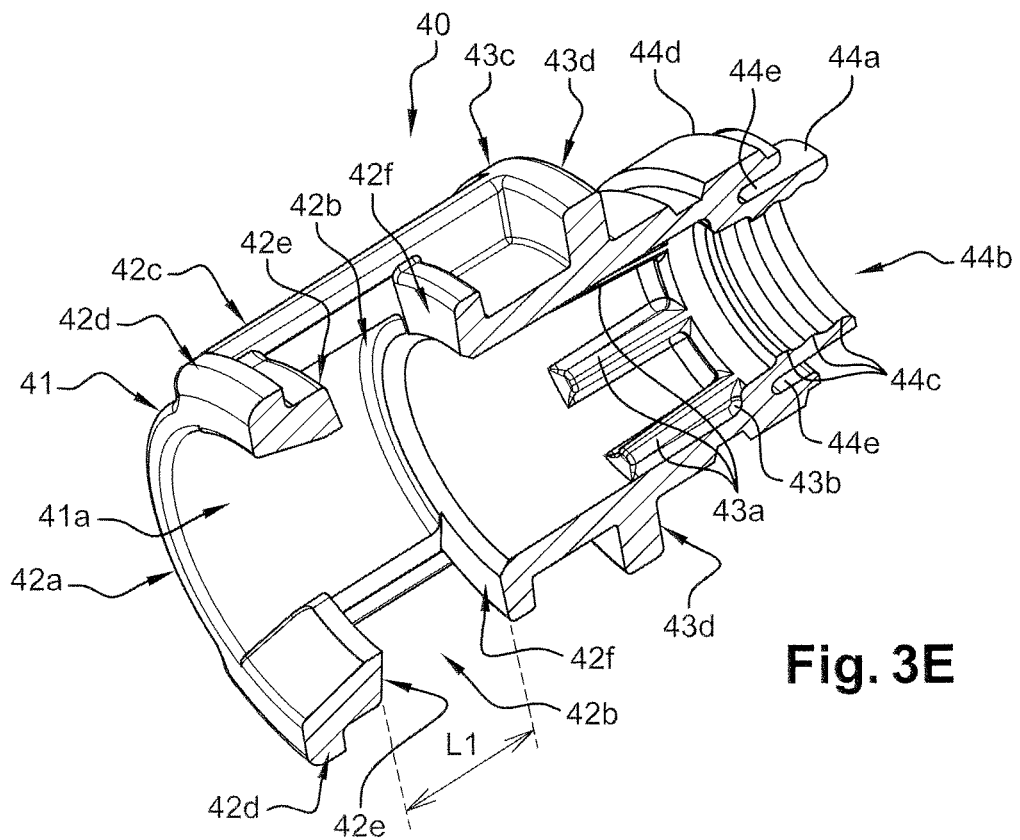
FIG. 3E is a cross-section perspective view of the rigid outer cap of the tip cap assembly of FIGS. 2A and 2B.

As shown in FIGS. 2A-2C, the syringe 10 may be sealingly closed by a tip cap assembly 30. This tip cap assembly 30 includes a rigid outer cap 40 which receives an elastomeric inner cap 50.

The rigid outer cap 40 will now be described with references to FIGS. 3A-3E.

The rigid outer cap 40 includes an essentially tubular wall 41 having a longitudinal axis A' and defining a cavity 41a open on both distal and proximal ends. The tubular wall 41 includes three different portions: a distal portion 42, a central portion 43 and a proximal portion 44.

The distal portion 42 has an essentially tubular shape and includes a distal opening 42a and two longitudinal windows 42b (see FIG. 3E, only one visible in FIGS. 3A and 3B), diametrically opposed, in the example shown. Each window 42b is enclosed on its outside by two longitudinal ribs 42c and one distal radial rib 42d and on its inside by two abutment surfaces 42e and a shoulder 42f. In other aspect (not shown), one, three or four abutment surfaces 42e are provided into the rigid cap 40. A length L1, measured along axis A', is defined between the abutment surfaces 42e and the shoulder 42*f* and consists in the longitudinal dimension of the longitudinal windows 42*b*. The shoulder 42*f* is located between the distal portion 42 and the central portion 43. In other aspects (not shown), the distal portion 42 includes one, three or four windows 42*b*.

The central portion 43 has an essentially tubular shape and includes on the inside a plurality of longitudinal rims 43*a* linked with a shoulder 43*b*. On the outside, a ring 43*c* including a proximal abutment surface 43*d* is linked with two longitudinal ribs 43*e* and the longitudinal ribs 42*c*. The longitudinal ribs 43*e* only extend along part of the central portion 43 while the longitudinal ribs 42*c*, enclosing the windows 42*b*, extend along both the distal portion 42 and part of the central portion 43. The shoulder 43*b* is located between the central portion 43 and the proximal portion 44.

The proximal portion 44 has an extension having the shape of a truncated cone or frustoconical extension 44*a*. The frustoconical extension 44*a* includes a proximal opening 44*b* and three annular ridges 44*c*. On the outside, an outer thread 44*d* extends from the ring 43*c* of the central portion 43 and is separated from the frustoconical extension 44*a* by a radial recess 44*e*. In another aspect (not shown), the rigid cap 40 is not provided with an outer thread 44*d* and the proximal portion 44 only includes a frustoconical extension 44*a* with ridges 44*c*. This aspect can then be used with a syringe 10 that is not provided with a collar 20.

The rigid outer cap can be made of a rigid polymer such as polypropylene, polyethylene, polyvinylchloride, polystyrene, polycarbonate or a copolymer such as acrylonitrile butadiene styrene or styrene acrylonitrile.

Figure 4A:
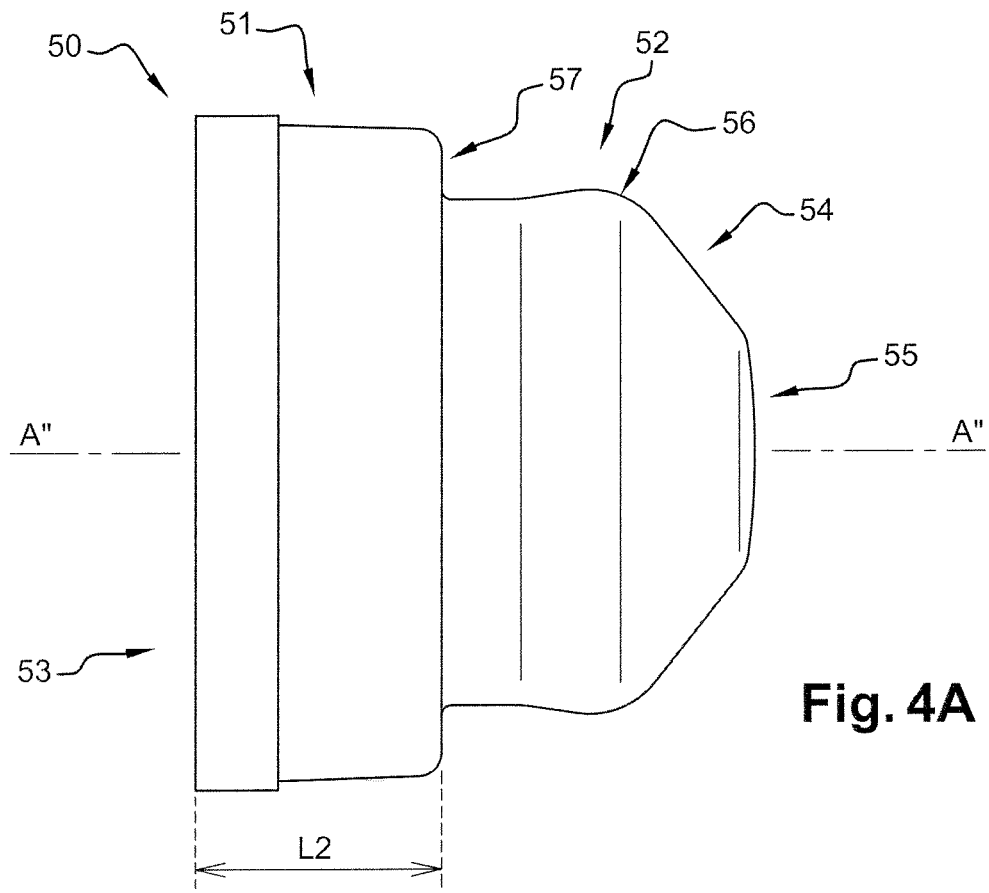
FIG. 4A is a side view of the elastomeric inner cap of the tip cap assembly of FIGS. 2A and 2B.
Figure 4B:
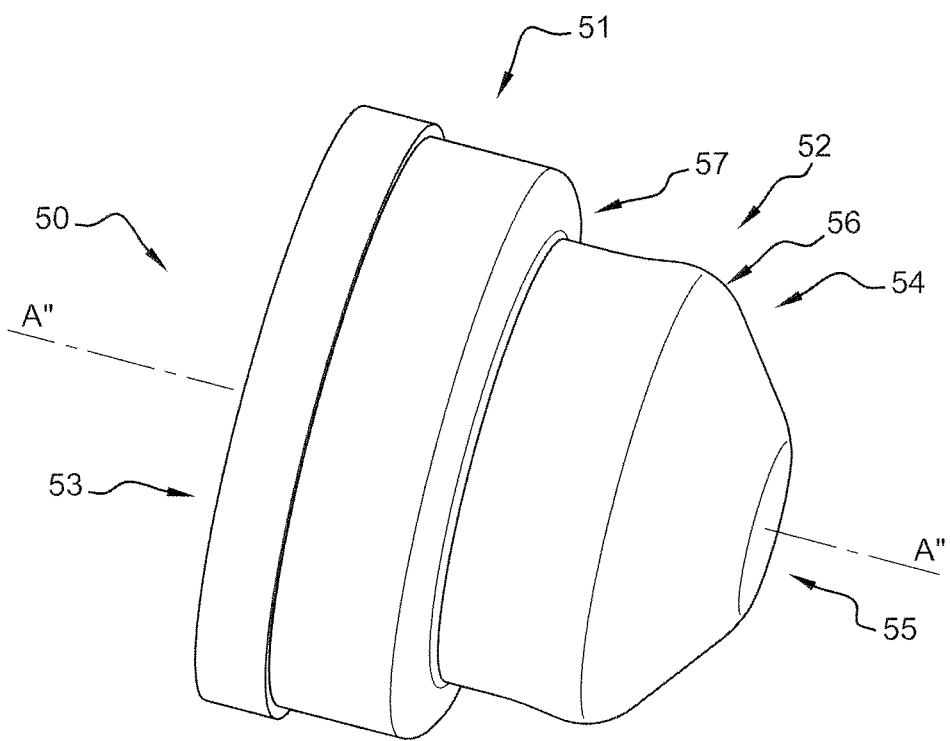
FIG. 4B is a perspective view of the elastomeric inner cap of the tip cap assembly of FIGS. 2A and 2B.

The elastomeric inner cap 50 will now be described with reference to FIGS. 4A and 4B. It includes a distal portion 51 and a proximal portion 52 both having a longitudinal axis A". The distal portion 51 has an essentially cylindrical shape and a flat distal face 53. The proximal portion 52 includes a frustoconical protrusion 54 having the shape of a truncated cone, a proximal face 55 essentially perpendicular to the axis A" and a circular bump 56. The proximal portion 52 has a smaller average diameter than the distal portion 51 and a radial rim 57 is located at the connection between the proximal portion 52 and the distal portion 51. Preferably the cone angle α of the truncated cone forming the frustoconical protrusion 54 ranges from 40° to 60° relative to axis A", more preferably is 50° relative to axis A". The length L2 of the distal portion 51, measured along axis A", is defined between the radial rim 57 and the flat distal face 53. In the aspect of FIGS. 4A and 4B, the proximal face 55 is essentially flat. In other aspects (not shown), the proximal face 55 has a curvature radius, the center of which being situated on the axis A". The diameter of the proximal face 55 is preferably greater than the diameter of the fluid passageway 14 of the distal tip 13. As appears from FIGS. 4A and 4B, the proximal face 55 is the most proximal face of the elastomeric inner cap 50.

The elastomeric cap 50 is able to adopt three different configurations: a free configuration when it is not assembled with the rigid cap 40, a first stressed configuration when it is assembled into the rigid cap 40 to form the tip cap assembly 30 and a second stressed configuration due to the distal pressure applied by the distally projecting tip 13 when the tip cap assembly 30 closes the fluid passageway 14 of an injection system 10, as will be explained later.

Suitable materials for the elastomeric cap 50 of the invention include natural rubber, acrylate-butadiene rubber, cis-polybutadiene, chloro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

Figure 5:
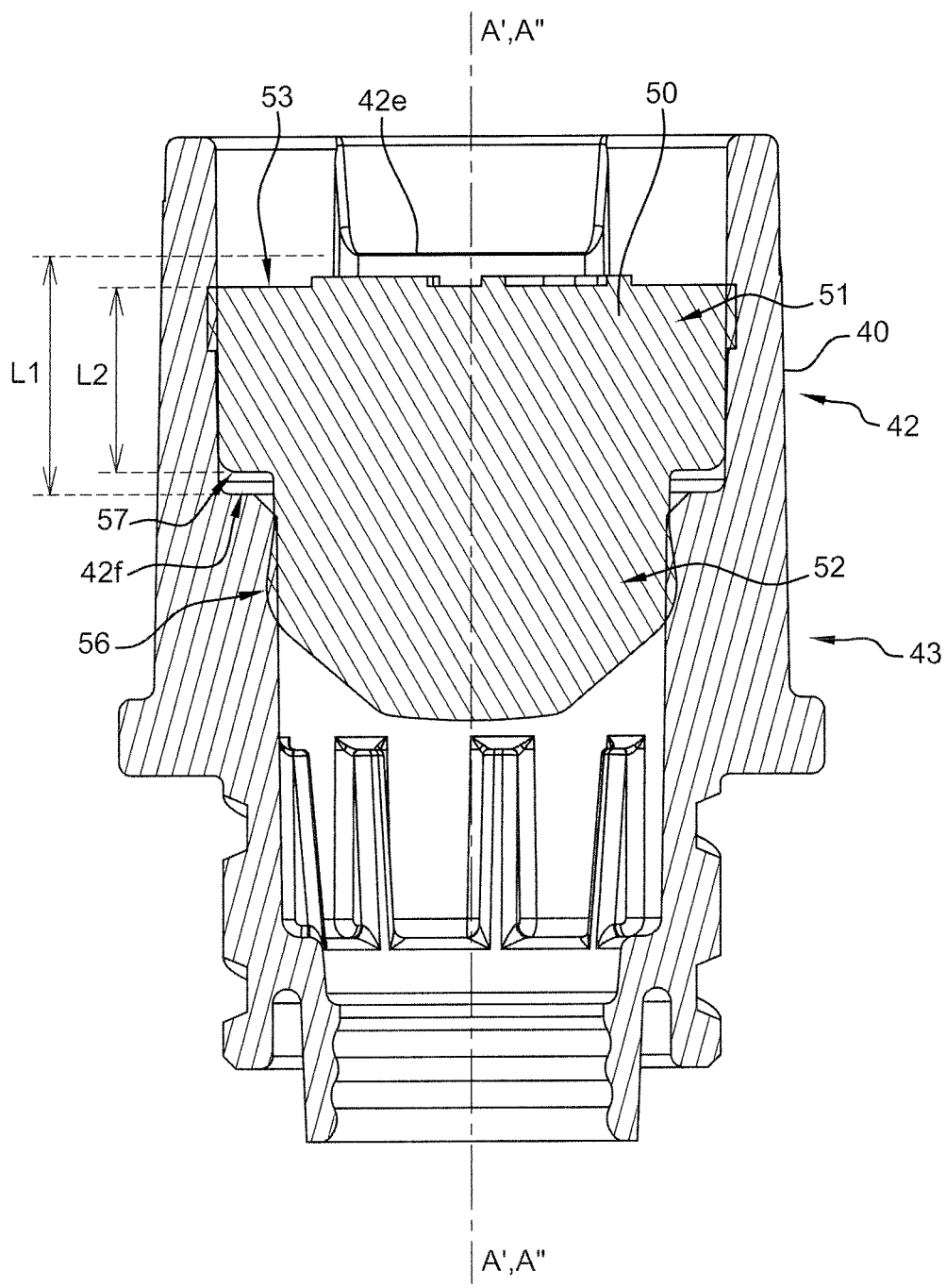
FIG. 5 is the theoretical superimposition of the rigid outer cap of FIGS. 3A, 3B and 3C on the elastomeric inner cap of FIGS. 4A and 4B.

The superposition of cross-sectional views of the elastomeric inner cap 50 (FIGS. 4A-4B) and the rigid outer cap 40 (FIGS. 3A-3E) is shown as a theoretical view in FIG. 5, as the represented shape of the elastomeric inner cap 50 on this Figure is that of its free configuration and therefore overlaps (at circular bump 56) the shape of the rigid outer cap 40. The distal portion 51 of the elastomeric inner cap 50 is intended to be received in the distal portion 42 of the rigid cap 40, and the proximal portion 52 of the elastomeric inner cap 50 is intended to be received in the central portion 43 of the rigid cap 40. In the theoretical view of FIG. 5, the axis A' of the rigid cap 40 is superposed with the axis A" of the elastomeric inner cap 50 and the length L1 included between the abutment surface 42*e* and the shoulder 42*f* is slightly greater than the length L2 of the distal portion 51 of the elastomeric inner cap 50. In another aspect (shown in FIG. 7), the length L1 is equal to the length L2 of the distal portion 51. In a last aspect (not shown), the length L1 is slightly smaller in comparison to the length L2. Finally, the circular bump 56 of the elastomeric inner cap 50 has a diameter slightly greater than the internal diameter of the central portion 43 of the rigid cap 40.

Figure 6A:
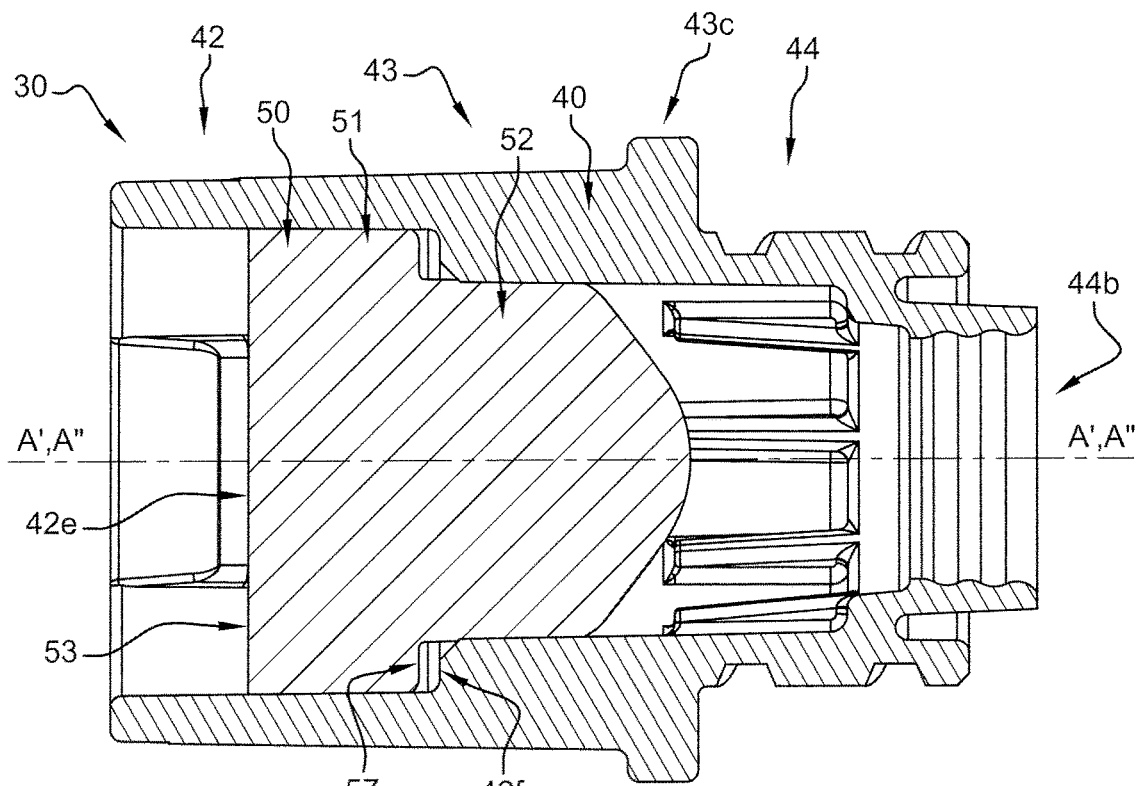
FIG. 6A is a cross-section view of a tip cap assembly according to an aspect of the present disclosure.
Figure 6B:
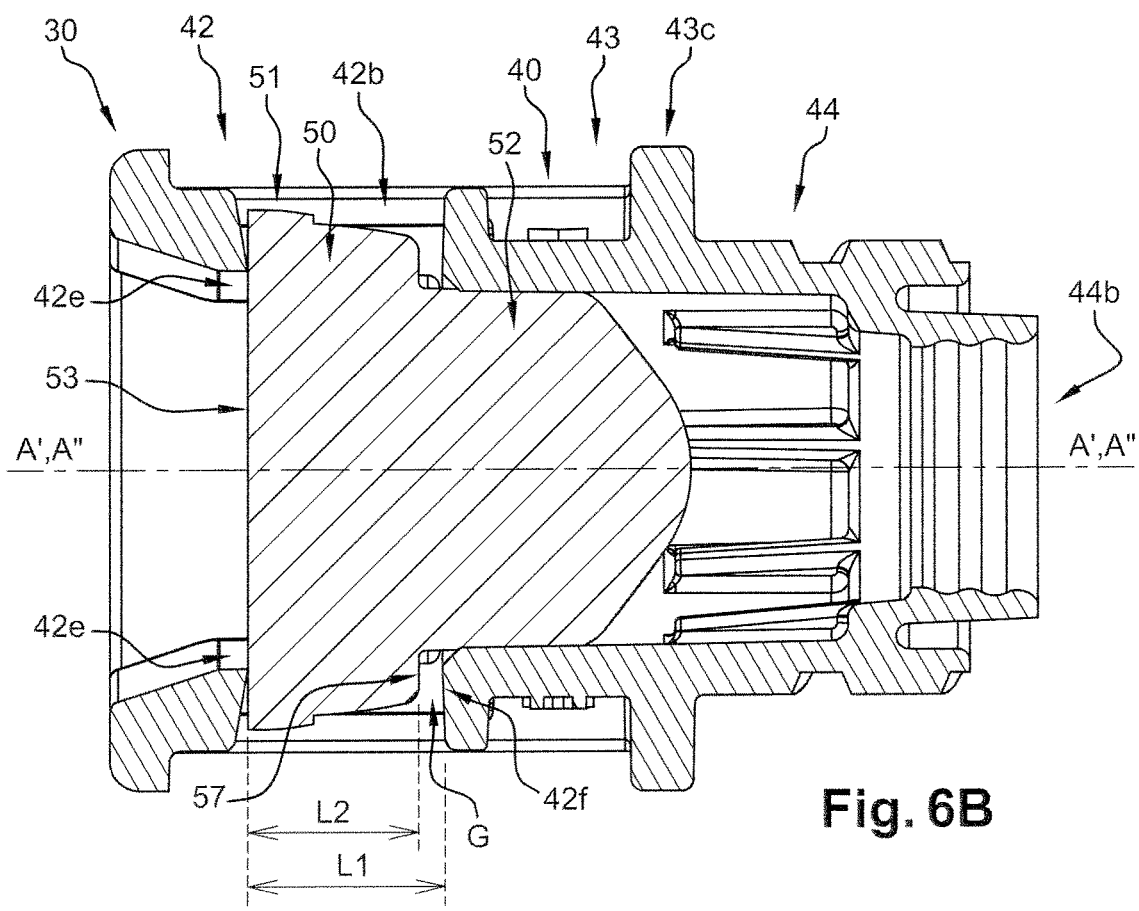
FIG. 6B is a cross-section view of a tip cap assembly according to another aspect of the present disclosure.

A tip cap assembly 30 ready to be used, with the elastomeric inner cap 50 assembled into the rigid cap 40, is shown in FIGS. 6A and 6B. The elastomeric inner cap 50 is maintained inside the rigid cap 40 and is in its first stressed configuration: its distal portion 51 is enclosed between the abutment surface 42*e* and the shoulder 42*f* of the rigid cap 40 and its longitudinal axis A" is superposed with the longitudinal axis A' of the rigid cap 40. The elastomeric inner cap 50 is distally blocked by the contact between its distal face 53 and the abutment surfaces 42*e* of the rigid cap 40, and proximally blocked by the contact between its radial rim 57 and the shoulder 42*f* of the rigid cap 40. In the embodiment of FIGS. 6A and 6B, the length L1 is greater than the length L2 and a gap G exists between the rigid cap 40 and the elastomeric cap 50 which allows a limited translation of the elastomeric cap 50 within the rigid cap 40. In the embodiments where L1 is equal to or smaller than L2, the abutment surfaces 42*e* of the rigid cap 40 contact directly the distal face 53 of the elastomeric inner cap 50 while the shoulder 42*f* of the rigid cap 40 contacts the radial rim 57 of the elastomeric cap 50. Consequently, the radial rim 57 contacts the shoulder 42*f* at least when a proximal pressure is applied on the elastomeric inner cap 50, while the abutment surfaces 42*e* contact the distal face 53 at least when a distal pressure is applied on the elastomeric inner cap 50. The abutment surfaces 42*e* and the shoulder 42*f* of the rigid cap 40, together with the distal face 53 and the radial rim 57 therefore form holding means to secure the elastomeric inner cap 50 within the rigid cap 40.

Figure 7:
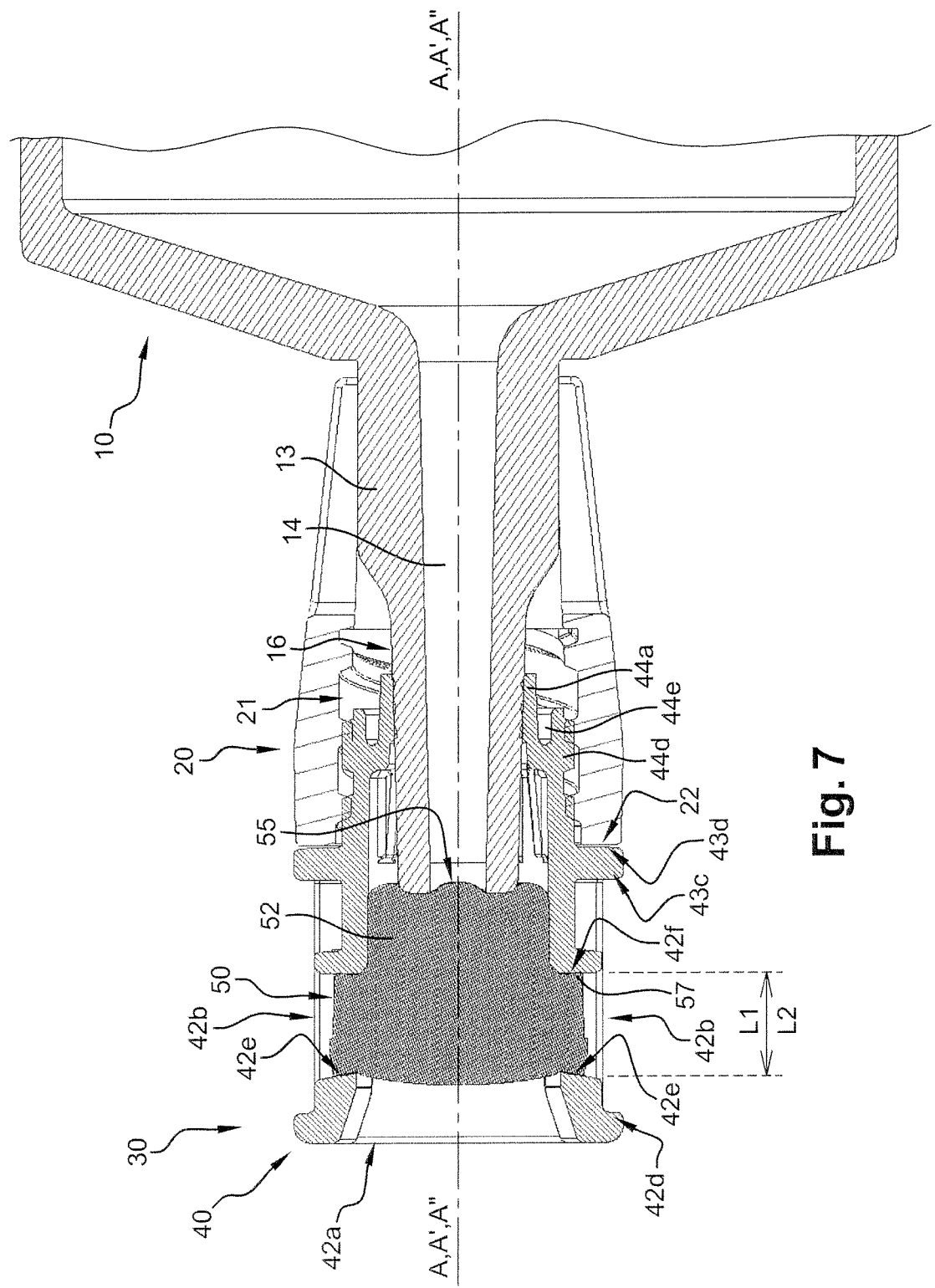
FIG. 7 is a cross-section view of a tip cap assembly mounted on the syringe of FIGS. 1A, 1B and 1C.

Furthermore, the average diameter of the distal portion 51 of the elastomeric inner cap 50 is chosen to be slightly larger than the inside diameter of the distal portion 42 of the rigid cap 40. As a result, the elastomeric inner cap 50 is tightened on its diameter, is slightly deformed, and part of this elastomeric inner cap 50 even protrudes further through the windows 42*b* of the rigid cap 40 when assembled (as shown in FIG. 7). This deformation thus enhances the contact area between the abutments surfaces 42*e* and the distal face 53 of the elastomeric inner cap 50. Similarly, and as shown in FIG.

5, the circular bump 56 of the proximal portion 52 has a diameter slightly larger than the inside diameter of the central portion 43 of the rigid cap 40. Consequently, the proximal portion 52 is tightened on its whole diameter, and the frustoconical protrusion 54 is deformed over its length, thus further extending toward the proximal portion 44 of the rigid cap 40. These deformations further contribute to maintain the elastomeric inner cap 50 in the rigid cap 40. In the aspect where L1 is smaller than L2 (not shown), the distal portion 51 of the elastomeric cap 50 is tightened on its length and slightly deformed.

Due to the specific shape of the rigid cap 40 and the elastomeric inner cap 50, the assembly of the tip cap 30 can be obtained by aligning the axis A' of the rigid cap 40 with the axis A" of the elastomeric inner cap 50, the proximal portion 52 of the elastomeric inner cap 50 facing the distal opening 42a of the rigid cap 40. A proximal pressure applied on the elastomeric inner cap 50, or a distal pressure applied on the rigid cap 40 allows the introduction and the slight deformation of the elastomeric inner cap 50 into the rigid cap 40. This operation can be facilitated by lubrication of the elastomeric inner cap 50, lubrication of the cavity 41a of the rigid cap 40, or both. In the aspect where L1 is greater than L2, the gap leads to a simpler assembling by allowing a greater deformation of the elastomeric cap 50 and permitting to have higher ranges of manufacturing tolerances. The tip cap assembly 30 of the present aspect is therefore very fast to assemble and the probability of an incorrect assembling is very limited.

The tip cap assembly 30 is now ready to be connected with a syringe 10 as shown in FIG. 7. The axis A', A" of the tip cap assembly are aligned with the axis A of the syringe 10, the proximal opening 44b of the tip cap assembly 30 facing the distally projecting tip 13 of the syringe 10. When the tip cap assembly 30 is provided with an outer thread 44d, a rotational movement is required to screw the outer thread 44d into the inner thread 21 of the collar 20 of the syringe 10. Before the end of the rotation, the projecting tip 13 comes in contact with the proximal face 55 of the elastomeric inner cap 50. In the aspect where L1 is greater than L2, the elastomeric cap 50 is pushed against the abutment surfaces 42e of the rigid cap 40 and then progressively compressed. In the aspects where L1 is equal or smaller than L2, the elastomeric cap 50 is already immobilized inside the rigid cap 40 and is directly compressed by the projecting tip 13. Thereafter, the lateral surface 16 of the projecting tip 13 comes in contact with the frustoconical extension 44a, which is progressively deformed radially outwardly. At the end of the rotation, the proximal abutment surface 43d of the tip cap assembly 30 comes in contact with the distal rim 22 of the collar 20. Thus, the tip cap assembly 30 is secured to the collar 20 and to the distally projecting tip 13 as shown in FIGS. 2A, 2B and 7. The proximal abutment surface 43d of the rigid cap 40 cooperates with the distal rim 22 of the collar 20 to prevent any further rotational movement that would damage the tip cap assembly 30. This cooperation also ensures the correct positioning of the tip cap 30 with respect to the collar 20 and provides the user with a tactile indication that the syringe 10 is hermetically sealed. In another aspect (not shown), the proximal abutment surface 43d is not present on the ring 43c but integrated on the outer surface of the rigid cap 40.

In an aspect where the syringe 10 is not provided with a collar 20 and the tip cap assembly 30 is consequently not provided with an outer thread 44d or a ring 43c (not shown), the tip cap assembly 30 is simply mounted on the distally projecting tip 13 by a proximal movement.

As shown in FIG. 7, the elastomeric inner cap 50 does not substantially penetrate the fluid passageway 14 since the diameter of the proximal face 55 is at least greater than the diameter of the fluid passageway 14. When the tip cap assembly 30 is plugged on the tip, the elastomeric inner cap 50 is compressed between the distally projecting tip 13 and the abutment surfaces 42e of the rigid cap 40, which significantly deforms the proximal portion 52 of the elastomeric inner cap 50 in order to ensure the tight sealing of the fluid passageway 14. Part of this deformation is absorbed by the specific shape of the frustoconical protrusion 54 of the elastomeric cap 50, which contributes to limit both axial and radial stress transmitted to the rigid cap 40. The deformation of the elastomeric cap 50 is also partially allowed by the distal opening 42a and the longitudinal windows 42b of the rigid cap 40, as shown in FIG. 7, further reducing the amount of axial stress transmitted to the rigid cap 40 through the abutment surfaces 42e. The frustoconical protrusion 54 of the elastomeric inner cap 50 as well as the distal opening 42a and the longitudinal windows 42b of the rigid cap 40 therefore constitute stress-limiting means that allow the elastomeric cap 50 to be substantially deformed when the tip cap assembly 30 closes the passageway 14 of the syringe 10. Unintended deformation of the rigid cap 40 and in particular of its distal portion 42, due to the stress resulting of the compression of the elastomeric cap 50 over time, is therefore avoided: the syringe can be kept perfectly sealed during storage time. Thanks to the appropriate connection of the tip cap assembly with the projecting tip 13, neither the nature nor the quality, for example the purity, of the fluid stored inside the syringe is altered, even after an extended period of storage. Wastage of valuable fluids is therefore avoided, as well as unacceptable risks for patients and medical staff that would be in contact with the fluid. The specific geometry of the rigid cap 40, and in particular the distal opening 42a, the windows 42b, the abutment surfaces 42e, as well as the specific geometry of the elastomeric inner cap 50 and in particular, the frustoconical protrusion 54, therefore allow a hermetical and sustainable sealing of the projecting tip 13 of the syringe 10.

The rigid cap 40 is reinforced on its outside by the longitudinal ribs 43e, the longitudinal ribs 42c and the distal radial ribs 42d and on its inside by the longitudinal rims 43a and the shoulder 43b, in order to resist against any deformation that might result from the stress transmitted by the elastomeric inner cap 50 when the tip cap assembly 30 closes the fluid passageway 14, or by the user while manipulating the tip cap assembly. Longitudinal ribs 43e, the longitudinal ribs 42c, the distal radial ribs 42d, the longitudinal rims 43a and the shoulder 43b therefore constitute reinforcement means.

In the aspect where L1 is greater than L2, the gap G between the rigid cap 40 and the elastomeric cap 50 is also useful to be compatible with different kinds of syringes showing unconventional lengths of distally projecting tip 13, for example syringes that have not been designed according to usual standards. As a result, the tip cap assembly 30 according to this specific aspect can provide an optimal and sustainable sealing even in the case of non-standard syringes.

In the closed position shown in FIG. 7, the radial recess 44e allows a limited radial deformation of the frustoconical extension 44a due to the contact with the lateral surface 16 of the distally projecting tip 13. As a result, the frustoconical extension 44a extends around and hermetically seals the distally projecting tip 13, the three annular ridges 44c being in tight contact with its lateral surface 16. This ensures the circumferential sealing of the lateral wall 16 of the distal tip 13 and allows the sterile maintenance of the cavity 41a of the tip cap assembly 30 and therefore the projecting tip 13 of the syringe 10. In addition, the circumferential sealing of the lateral wall 16 of the distal tip 13 is performed even when the distal tip 13 is not perfectly circular. A distal tip 13 showing a limited asymmetry or a ellipsoidal section resulting of manufacturing tolerances does not deteriorate the sterility of the cavity 41a of the tip cap assembly 30. The frustoconical extension 44a therefore acts as a sterility skirt during the storage time of a prefilled syringe and significantly limits or eliminates migration of contaminants from the projecting tip to the fluid before and during the step of injection to a patient. In other aspects (not shown), the sterility skirt 44a is provided with at least one annular ridge 44c.

At the end of the storage time, immediately before injecting the fluid stored to a patient, a limited effort is required to unscrew the tip cap assembly 30 from the collar 20 and thus to open the fluid passageway 14 of the syringe 10. Indeed, the specific shape of the frustoconical protrusion 54 of the tip cap assembly 30 limits the area of contact between the elastomeric cap 50 and the distally extending tip 13 to the distal surface 15, therefore avoiding any contact between the elastomeric inner cap 50 and the lateral surface 16 or the fluid passageway 14 of the distally extending tip 13. This significantly reduces or cancels the sticking phenomenon that may happen after an extended storage period and therefore allows a quick and easy removal of the tip cap assembly 30. The fluid passageway 14 is also maintained clean of particles since the frustoconical protrusion 54 does not contact directly the inside surface of the fluid passageway 14. During the opening of a syringe 10, the frustoconical protrusion 54 of the elastomeric inner cap 50 also creates a spring effect to the tip cap assembly 30 which further contributes to an easy removal. Finally, reinforcement means 43e, 42c, 42d, 43a and 43b allow for a thinner tubular wall 41 of the rigid cap 40. The deformation of the rigid cap 40 during the removal step is therefore limited, which again ensures an easy removal. The tip cap assembly according to the present disclosure therefore can reduce economic loss by preventing discarding prefilled syringes before use. Furthermore, injection can be done at very short notice and without excessive effort. This could save patients requiring immediate treatment.

Figure 8:
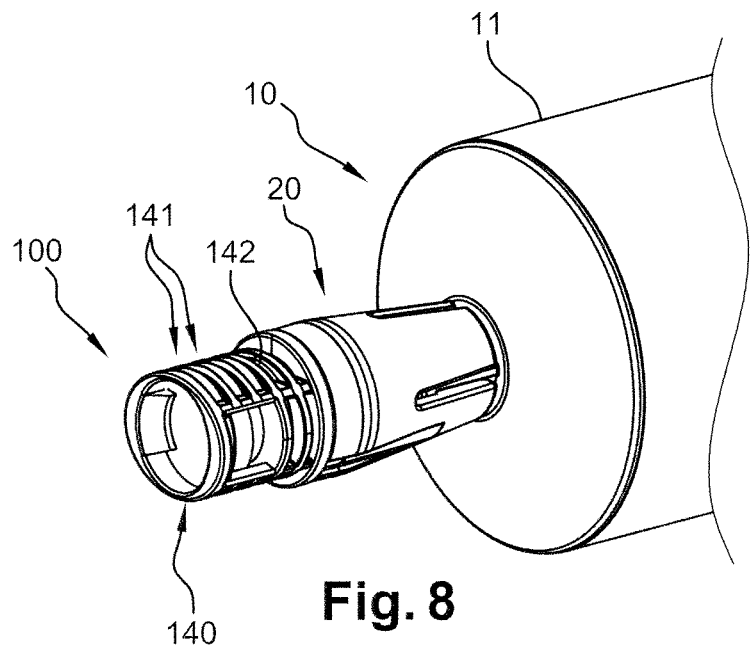
FIG. 8 is a perspective view of the syringe of FIGS. 1A-1C closed by a tip cap assembly according to an aspect of the present disclosure.

In another aspect shown in FIG. 8, the tip cap assembly 100 has the global shape of an elliptic cylinder and includes elliptical reinforcement ridges 141 and 142 on the outer surface of the rigid cap 140, the proximal portion (not visible) of the rigid cap 140 being substantially cylindrical to fit within the syringe collar 20 and all other features being similar to those previously described for the tip cap assembly 30 of FIGS. 1-7. Comparing to the circular cylinder tip cap assembly 30, the tip cap assembly 100 is easier to screw or remove from the syringe collar 20 as the elliptical shape provides more contact surface to the user's fingers, leading to a better gripping ability.

Figure 9:
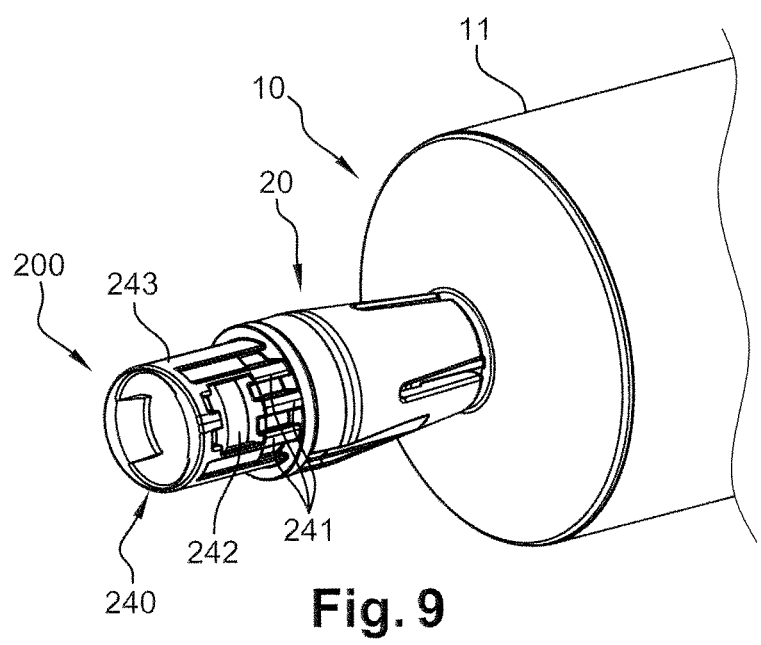
FIG. 9 is a perspective view of the syringe of FIGS. 1A-1C closed by a tip cap assembly according to another aspect of the present disclosure.

In another aspect shown in FIG. 9, the tip cap assembly 200 has globally the shape of an elliptical cylinder and the outer surface of the rigid cap 240 is provided with longitudinal reinforcement ridges 241 surrounding the windows 242 (only one visible in FIG. 9), and two flat surfaces 243 placed between the windows 242. The proximal portion (not visible) of the rigid cap 240 is substantially cylindrical to fit within the syringe collar 20 and all other features are similar to those previously described for the tip cap assembly 30 of FIGS. 1-7. Comparing to the circular cylinder tip cap assembly 30, the tip cap assembly 200 is easier to screw or remove from the syringe collar 20 as the elliptical shape provides more contact surface to the user's fingers, leading to a better gripping ability.

In other aspects (not shown), the tip cap assembly 30 can be provided with a tamper evidence feature, for example in the form of breakable tabs between the collar 20 and the ring 43c of the rigid cap 40. In other aspects (not shown), the tamper evidence features also include a security ring provided on the collar 20.

Thanks to its unique structure, the tip cap assemblies according to the present disclosure allows maintaining a perfect sealing overtime, protecting the syringe tip from contamination during storage time and providing an opening with limited effort.

The invention claimed is:

1. A tip cap assembly adapted to close a fluid passageway of a distally projecting tip of an injection system, said tip cap assembly comprising:
    an elastomeric inner cap having a frustoconical protrusion extending proximally, said frustoconical protrusion having a proximal-most face,
    a rigid outer cap which is securely disposed around said elastomeric inner cap,
    wherein the proximal-most face of the frustoconical protrusion has a diameter at least greater than a diameter of a distal-most opening of the fluid passageway of the injection system, and
    wherein the proximal-most face of the frustoconical protrusion extends in a direction substantially perpendicular to a longitudinal axis of the fluid passageway of the injection system.

2. The tip cap assembly according to claim 1, further provided with a stress-limiting element for allowing said elastomeric inner cap to be substantially deformed when the assembly closes said fluid passageway.

3. The tip cap assembly according to claim 2, wherein said stress-limiting element comprises at least one window provided onto said rigid outer cap.

4. The tip cap assembly according to claim 3, wherein the at least one window comprises two diametrically opposed longitudinal windows provided onto said rigid outer cap.

5. The tip cap assembly according to claim 2, wherein said stress-limiting element comprises a distal opening provided into said rigid outer cap.

6. The tip cap assembly according to claim 1, wherein the elastomeric cap and the outer rigid cap comprises a holding element to secure said elastomeric inner cap into said rigid outer cap.

7. The tip cap assembly according to claim 6, wherein said holding element comprises a shoulder provided into the rigid outer cap, and a radial rim provided onto the elastomeric inner cap, said elastomeric inner cap being proximally blocked by the contact between said radial rim and said shoulder.

8. The tip cap assembly according to claim 6, wherein said holding element comprises at least one abutment surface provided into the rigid outer cap, and a distal face provided onto the elastomeric inner cap, said elastomeric inner cap being distally blocked by the contact between said abutment surface and said distal face.

9. An injection system comprising a longitudinal barrel, a distally projecting tip provided with a fluid passageway extending therethrough, a distal surface and a lateral surface, wherein said injection system further comprises a tip cap assembly according to claim 1.

10. An injection system including a longitudinal barrel, a distally projecting tip and a tip cap assembly, said distally projecting tip being provided with a fluid passageway extending therethrough, a distal surface and a lateral surface, said tip cap assembly comprising:
an elastomeric inner cap having a frustoconical protrusion,
a rigid outer cap which is securely disposed around said elastomeric inner cap,
wherein said tip cap assembly is configured so that, when said tip cap assembly closes said fluid passageway, a proximal-most face of said frustoconical protrusion contacts said distally projecting tip only at the distal-most surface, wherein the proximal-most face of the frustoconical protrusion extends in a direction substantially perpendicular to a longitudinal axis of the fluid passageway.

11. The injection system according to claim 10, further comprising a collar securely engaged around said distal tip, having an inner thread and a distal rim, and wherein said rigid outer cap is provided with an outer thread to cooperate with the inner thread in order to close said passageway.

12. The injection system according to claim 11, wherein the rigid outer cap is provided with a proximal abutment surface contacting the distal rim of said collar when said tip cap assembly closes said passageway.

13. An injection system comprising:
a longitudinal barrel,
a distally projecting tip,
a collar provided with an inner thread,
said collar being securely engaged around said distally projecting tip, said distally projecting tip having a lateral surface and a fluid passageway extending therethrough, and
a tip-cap assembly comprising an elastomeric inner cap, and a rigid outer cap that is securely disposed around said elastomeric inner cap,
wherein said rigid outer cap of the tip cap assembly comprises:
an outer thread intended to be screwed with the inner thread of the collar,
a frustoconical extension,
a radial recess between the outer thread and the frustoconical extension,
wherein said frustoconical extension ensures a circumferential sealing of the distally projecting tip around the lateral surface in order to act as a sterility skirt when the tip-cap assembly closes the passageway of the projecting tip.

14. The injection system according to claim 13, wherein the frustoconical extension is provided with at least one annular ridge.

15. A tip-cap assembly adapted to close a fluid passageway of a distally projecting tip of an injection system, said tip-cap assembly comprising:
an elastomeric inner cap having a distal face and a radial rim, and a length L2 defined as a distance between the distal face and the radial rim,
a rigid outer cap configured to be securely disposed around said elastomeric inner cap, said rigid outer cap comprising a shoulder and at least one abutment surface, and a length L1 defined as a distance between the at least one abutment surface and the shoulder,
wherein the elastomeric inner cap is distally blocked by contact between the distal face and the at least one abutment surface and proximally blocked by contact between the radial rim and the shoulder,
and wherein the length L1 is greater than the length L2 in order to allow a limited translation of the elastomeric inner cap within the rigid outer cap.

* * * * *